United States Patent
Yamada et al.

(10) Patent No.: US 6,332,361 B1
(45) Date of Patent: Dec. 25, 2001

(54) METHOD FOR EVALUATING BONDING PROPERTIES OF A METALLIC PIPE

(75) Inventors: Ryuzo Yamada, Chita; Hirotsugu Horio, Tokai; Takao Shimizu, Nogoya, all of (JP)

(73) Assignee: Daido Tokushuko Kabushiki Kaisha, Aichi (JP)

( * ) Notice: Subject to any disclaimer, the term of this patent is extended or adjusted under 35 U.S.C. 154(b) by 0 days.

(21) Appl. No.: 09/417,909

(22) Filed: Oct. 13, 1999

(30) Foreign Application Priority Data

Oct. 14, 1998 (JP) .................................. 10-291650
Jun. 28, 1999 (JP) .................................. 11-181639
Aug. 24, 1999 (JP) .................................. 11-237033

(51) Int. Cl.$^7$ .................................................. G01N 29/00
(52) U.S. Cl. ................................ 73/627; 73/598; 73/599; 73/600; 73/602
(58) Field of Search ........................ 73/627, 599, 622, 73/602, 598, 620, 628, 643, 600, 624

(56) References Cited

U.S. PATENT DOCUMENTS

| | | | |
|---|---|---|---|
| 3,552,191 | | 1/1971 | Heseding ............................. 73/624 |
| 3,791,199 | * | 2/1974 | Toth et al. ........................... 73/67.5 |
| 3,873,830 | * | 3/1975 | Forster ............................... 250/236 |
| 4,054,053 | * | 10/1977 | Yamamoto et al. ................... 73/67.8 |
| 4,088,029 | * | 5/1978 | Yamamoto et al. ................... 73/612 |
| 4,270,389 | * | 6/1981 | Shiraiwa et al. ...................... 73/612 |
| 4,395,911 | * | 8/1983 | Maceek ............................... 73/622 |
| 4,406,167 | * | 9/1983 | Maeda ................................. 73/622 |
| 4,522,064 | | 6/1985 | McMillan ............................ 73/592 |
| 4,760,737 | * | 8/1988 | Kupperman .......................... 73/622 |
| 4,843,884 | * | 7/1989 | House et al. ......................... 73/622 |
| 5,329,561 | | 7/1994 | Desruelles ........................... 376/245 |
| 5,439,157 | * | 8/1995 | Geier et al. .......................... 73/598 |
| 5,677,490 | * | 10/1997 | Gunther et al. ....................... 73/622 |
| 6,059,175 | * | 5/2000 | Hamada et al. ...................... 228/194 |
| 6,138,514 | * | 10/2000 | Iwamoto et al. ..................... 73/622 |

FOREIGN PATENT DOCUMENTS

| | | |
|---|---|---|
| 0 582 492 | 2/1994 | (EP) . |
| 60-82911 | 5/1985 | (JP) . |
| 8-62194 | 3/1996 | (JP) . |
| HEI 11-181638 | 6/1999 | (JP) . |

* cited by examiner

*Primary Examiner*—Hezron Williams
*Assistant Examiner*—Jacques Saint-Surin
(74) *Attorney, Agent, or Firm*—Finnegan, Henderson, Farabow, Garrett & Dunner, L.L.P.

(57) ABSTRACT

A method for evaluating bonding properties of a metallic pipe, the method comprises steps of measuring, in advance of a pipe expansion operation, at least one selected from a degree of shape discontinuity, a degree of defect at a bonding portion, and a degree of change in crystal structure, and comparing a measurement value with a predetermined threshold value to evaluate suitability of the bonding properties for applying pipe expansion.

17 Claims, 15 Drawing Sheets

METHOD FOR STEP FAULT MEASUREMENT

METHOD FOR REFLECTED ECHO MEASUREMENT

METHOD FOR TRANSMITTED ECHO

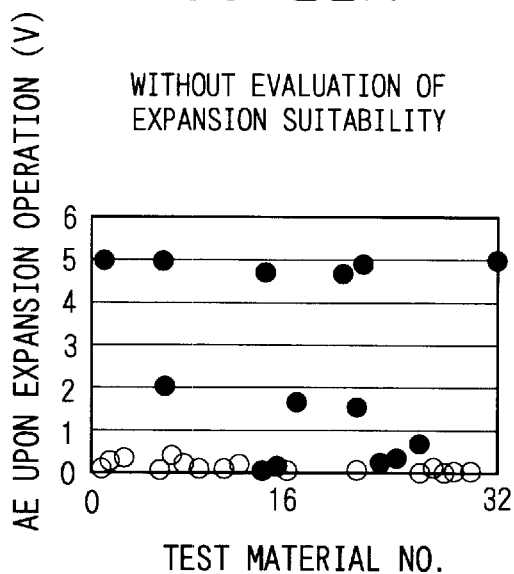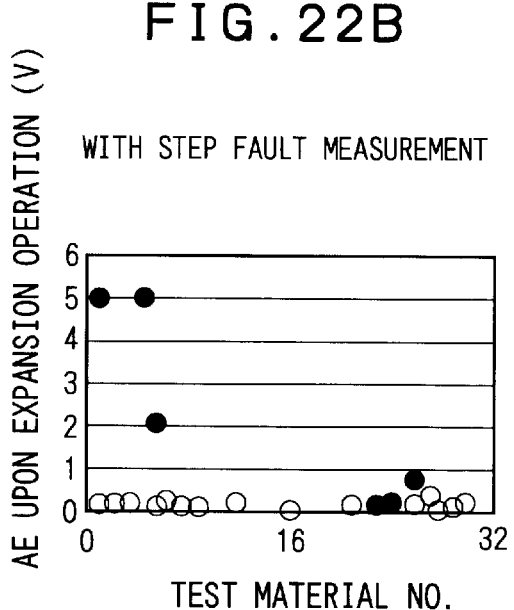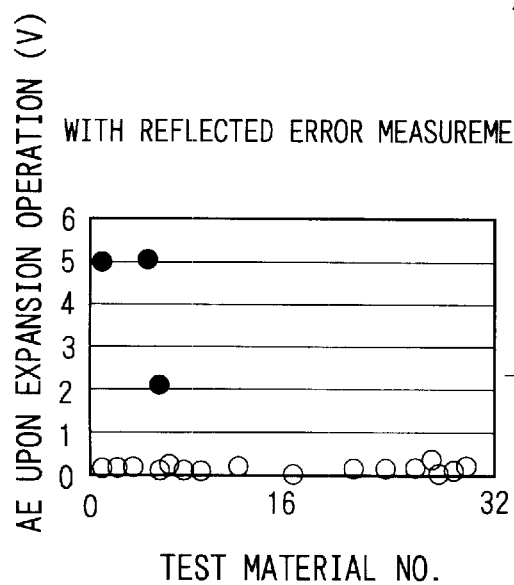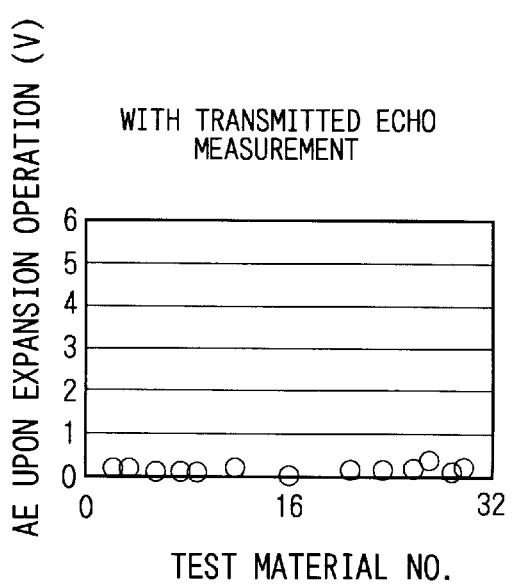

METHOD FOR EVALUATING BONDING PROPERTIES OF A METALLIC PIPE

BACKGROUND OF THE INVENTION

1. Field of the Invention

This invention relates to a method for evaluating bonding properties of a metallic pipe. More particularly, this invention relates to a method for non-destructively measuring a step fault and a defect produced at the bonding portion of a metallic pipe such as plant piping, a line pipe and an oil well pipe or the like, or for measuring a thickness of the bonding portion in order to evaluate, in advance of carrying out an pipe expansion operation to expand its diameter, if there is a possibility that a crack or the like might be produced at the bonding portion of the metallic pipe upon the pipe expansion operation.

2. Description of Related Art

Conventionally, in the technical fields such as a chemical industry and a petrochemical industry, some long metallic bonded pipes such as plant piping, a line pipe and an oil well pipe have been used until now in order to transport corrosive fluid over a long distance. For example, the pipe line is used for transporting crude oil obtained from an oil reservoir to an oil refining plant and the like and its length reaches a length in excess of over several tens of kilo-meters.

In addition, upon drilling an oil well, a steel pipe called a casing tube is buried in a down-hole to protect the down-hole drilled into the ground or prevent leakage of crude oil. Usually, the oil reservoir is at several thousand meters under the ground, so that it is necessary for the casing tube having a length of several thousand meters to reach the oil reservoir.

In turn, a seamless steel pipe having a superior corrosion resistance property is usually applied in a corrosive environment. However, a length of such a seamless steel pipe which is industrially produced in volume is about 10 to 15 m and the maximum limit of the length of such pipes possibly manufactured is about 100 m or so. Accordingly, the long metallic pipe such as a line pipe or an oil well pipe or the like is usually manufactured by joining a plurality of relatively short seamless steel pipes having a length of about 10 to 15 m or so.

As a method for joining metallic pipes to be applied for such applications as above, a screw joining method (a mechanical coupling method), a welding method (an orbital welding method), a friction welding method and a diffusion bonding method and the like are well known.

The screw joining method is a method in which metallic pipes are bonded together by screwing the end parts of the metallic pipes. The welding method is a method in which the metallic pipes provided with a groove at the end surface of each pipe are abutted against each other, and molten metal is filled in the grooves so as to bond the metallic pipes together.

On the other hand, as the diffusion bonding method, there are provided a solid phase diffusion bonding method and a liquid phase diffusion bonding method. In the diffusion bonding method, two metallic pipes are abutted directly to each other and elements are diffused while keeping a solid phases therebetween. In the liquid phase diffusion bonding method, an insert material is inserted into the bonding interface between the two metallic pipes, and then the insert material is melted to diffuse some of the elements at the metallic pipe.

The diffusion bonding method has some advantages that a joint obtained by this method has a superior property in strength and air-tightness compared to that of the screw joining method. Due to this reason, the diffusion bonding method is widely used as a method for connecting the metallic pipes such as an oil well pipe or line pipe and the like.

However, despite the advantage as described above that a high quality joint can be attained, the diffusion bonding method also has some disadvantages that bonding properties such as strength, toughness and the like greatly vary due to various kinds of defects produced at the bonding interface and the causes are found in a wide range. Especially, in the case where some defects such as cracks and poor bonding are produced at the edge of the bonding interface, they may cause a remarkable reduction in strength and fatigue properties of the bonded body due to a notch effect.

For example, there may be a case where the pipes are bonded together with the axes of the metallic pipes being inevitably misaligned from each other by the diffusion bonding method. In that case, a step fault is produced at the outer circumferential surface and/or inner circumferential surface of the bonding portion.

In addition, the metallic pipe industrially manufactured under in volume are usually with a predetermined size tolerance, and therefore there are variations in an outer diameter and a wall thickness of those metallic pipes are distributed within the range of the size tolerance. Due to this fact, even if the metallic pipes are bonded together under a state where their axes coincide with each other, a certain step fault is produced at the outer circumferential surface and/or the inner circumferential surface of the bonding portion.

In particular, in the case of bonding the metallic pipes by the liquid phase diffusion bonding method, the molten insert material may be squeezed out of the bonding portion and solidifies to produce a step fault there.

The step fault produced at the outer circumferential surface and/or inner circumferential surface of the bonding portion may be subjected to stress concentration which inevitably causes a connecting strength a fatigue properties to decline. For example, upon a pipe expansion operation, a pipe expansion tool is inserted into the metallic pipe and passes through the bonding portion in order to cause the plastic deformation there. At the time, a strong stress is applied to the bonding portion of the metallic pipes. Due to the strong stress, if a step fault is present at the inner circumferential surface of the bonding portion, the step fault may be subjected to a stress concentration which may cause to produce a crack at the bonding portion. In addition, when a step fault is produced at the inner circumferential surface of the bonding portion, corrosive substances may easily be accumulated there. As the result, the corrosion resistance and mechanical properties may be adversely influenced.

Also, in the case where a shape defect such as a crack is already present at the bonding portion, stress concentration occurs at the defect part, which may lead to produce a crack upon a pipe expansion operation. This is also true in the case where a metallic structural defect such as a poor diffusion of molten insert material at the base member is present, given that the aforesaid liquid phase diffusion bonding method is applied.

As to the step fault produced at the outer circumferential surface of the bonding interface, it can be easily detected by a visual inspection. Also, the defect produced at the outer circumferential surface of the bonding interface may be detected relatively easily by various kinds of non-destructive examinations such as an ultrasonic examination, a magnetic particle examination and a liquid penetrant examination or the like.

However, a step fault produced at the inner circumferential surface of the bonding interface is extremely difficult to be detected by a visual inspection. Further, there is no prior art to suggest or propose a method for detecting a step fault produced at the inner circumferential surfaces of the metallic pipes bonded by diffusion bonding without destruction of the pipes to be examined.

In addition, although the defect produced at the inner circumferential surface of the bonding interface may possibly be detected through various kinds of non-destructive examination method, there is no prior art to suggest an examination method to discriminate a step fault and a defect are reliably discriminated in the case where both step fault and defect are produced at the inner circumferential surface of the bonding interface, as well as to detect sizes of the step fault and defect with high accuracy.

Additionally, in the field of an oil well pipe, for example, in order to reduce a cost of drilling an oil well and to increase a production efficiency, an attempt has been made to expand a bonded body having a small diameter an inner diameter with the use of a mandrel or the like after it is buried in a drilled down-hole. However, if there is a step fault at the inner circumferential surface of the bonding portion, a stress is possibly concentrated at the step fault upon expanding the inner diameter by the mandrel or the like, which possibly produce a crack at the bonding portion.

In addition, there may be the cases where the crystal structure at the bonding portion undergoes increase in the grain size of the particles due to excessively high heating temperature during a diffusion bonding or where a diffusion bonding is insufficient without the occurrence of grain-coarsening due to an excessively low heating temperature or insufficient heating. In these cases, there is a possibility that a crack is produced at the grain boundaries or separation at the bonding portion of the metallic pipes upon pipe expansion.

If a plant or the like is assembled with the metallic pipes having a crack or a separation at the bonding portion, which have been over looked, production troubles at a site are inevitable. These troubles include that leakage of crude oil when a petroleum drilling is carried out in the case of applying such pipes as oil well pipes, or a gas leakage in the case of applying such pipes as pipe lines.

In addition, to replace the metallic pipe with a new metallic pipe or to repair a crack upon occurrences of a deficiency at the bonding portion of the metallic pipes, it requires tremendous amount of labor and expenditure for the repairing work.

Accordingly, in order to assure reliability in the resulting bonded properties of metallic pipes, it is important to measure a size of the step fault produced at the bonding portion quantitatively after bonding operation. In the prior art, such a measurement as described above has been carried out only on the outer surface of the bonding portion for the step fault produced outside with the use of slide calipers.

However, such a measurement of the step fault with the use of slide calipers has a problem that a large error may be produced if a size accuracy or surface flatness is poor as in the case of a seamless steel pipe. In addition, there is also a problem in the case where a step fault present at the bonding portion is wide, the number of measuring points must be increased and a large amount of measuring time is required to improve the accuracy of the measurement. Further, it is difficult to measure a step fault produced at the inner circumferential surface of the bonding portion with the slide calipers. In sort, there remains a problem that there is no means for performing an measurement of a step fault produced at the inner circumferential surface accurately and efficiently.

SUMMARY OF THE INVENTION

The present invention has been made in view of the above circumstances and has an object to overcome the above problems and to provide a method for evaluating quality of metallic bonded pipes in which presence of a step fault produced at the bonding portion of the metallic pipes bonded by a diffusion bonding process, in particular a step fault at the inner circumferential surface and its size can be detected in a non-destructive, high accurate and efficient manner.

It is another object of the present invention to provide a method for evaluating quality of metallic bonded pipes in which a step fault and a defect can be discriminated positively and sizes of the step fault and the defect can be detected in a non-destructive and high accurate manner in the case where both the step fault and defect are produced at the inner and/or outer circumferential surface of the bonding portion of the metallic pipes.

It is a still further object of the present invention to provide a method for evaluating quality of metallic bonded pipes in which a metallic bonded pipe having metallic pipes bonded to each other probably producing a crack or a defect at the bonding portion and separation at the bonded surface during expansion of a diameter of the pipe is eliminated in advance before starting the pipe expansion step.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, a method for evaluating bonding properties of a metallic pipe, the method comprises a first measurement step of measuring an echo height of an ultrasonic wave reflected back from an edge of a bonding interface where two pipe members are bonded together by diffusion bonding upon letting in an ultrasonic wave toward a first side of the bonding interface, a second measurement step of measuring an echo height of an ultrasonic wave reflected back from the bonding interface upon letting in the ultrasonic wave toward a second side of the bonding inter face, and a step fault determination step of determining whether or not there is a step fault present at the bonding interface based on a difference between the echo height measured in the first measurement step and the echo height measured in the second measurement step.

In accordance with the method for evaluating bonding properties of a metallic pipe of the first invention having the aforesaid configuration, an ultrasonic wave is made enter toward one side of the bonding interface and the reflected echo height reflected from the edge of the bonding interface is measured in the first measuring step. Similarly, an ultrasonic wave is made enter toward the other side of the bonding interface and the reflected echo height reflected from the edge of the bonding interface is measured in the second measuring step.

At this time, if there is a step fault present at the edge of the bonding interface, one pipe member is being protruded beyond the other pipe member. Due to this fact, the ultrasonic wave incident from the protruded pipe member toward the edge of the bonding interface is reflected at the protruded portion and a high reflected echo height is observed. Further, the reflected echo height becomes large in proportion to an area of the protruded portion.

In turn, the ultrasonic wave incident from the side of the pipe member not protruded toward the edge of the bonding interface merely passes through the bonding interface without being reflected, so that the reflected echo height within a noise echo level is observed. Accordingly, if a difference between the reflected echo heights measured in the first measuring step and in the second measuring step is obtained, presence of the step fault at the edge of the bonding interface and its size can be detected in a non-destructive manner with high accuracy.

As described above, in accordance with the present invention, there is an effect that whether or not a step fault is present at the edge of the bonding interface, in particular on the inner circumferential surface, can be discriminated based on a size of the difference between the reflected echo heights. In addition, the present invention has an effect that a protruding direction of the step fault can be easily discriminated based on a sign of a value indicating the difference between the reflected echo heights. Further, if a relation between the reflected echo height and the step fault measured on a sample under the same condition is obtained in advance, the present invention achieves another effect that a size of the step fault can be estimated with high accuracy based on a size of the difference of the reflected echo heights.

In the aforesaid invention, the method may further comprise a defect determination step of determining whether or not there is a defect present at said bonding interface based on minimum values of the echo height measured in the first measurement step and the echo height measured in the second measured step.

In this case, if both a step fault and a defect are present together at the edge of the bonding interface, an ultrasonic wave incident from the pipe member which is not protruded toward the edge of the bonding interface is reflected both at the protruded portion and the defect, so that high reflected echoes are observed.

On the other hand, an ultrasonic wave incident from the pipe member being protruded toward the edge of the bonding interface is reflected only at the defect. Thus, the reflected echo height corresponding only to the size of the defect is observed. Accordingly, measurement of the minimum values of the reflected echo height measured in the first measuring step and the second measuring step enables to detect presence of defect produced at the edge of the bonding interface as well as its size to be non-destructively with high accuracy through comparison of the minimum values with the noise echo level even in the case where a defect and a step fault are present together.

Further, even in the case where a step fault and a defect are present together at the edge of the bonding interface, a difference between the reflected echo heights measured in the first measuring step and the second measuring step corresponds to a size of the step fault. Thus, irrespective of presence of the defect, it is possible to detect presence of the step fault as well as its size non-destructively with high accuracy.

Still further, the present invention has an effect that a size of the defect can be estimated with high accuracy based on a size of the minimum values of the reflected echo heights even in the case where a step fault and a defect are present together through the relation between a reflected echo height and a defect measured on a sample under the same condition being obtained in advance.

The second invention of the present patent application in regard to the method for evaluating bonding properties of a metallic pipe, the method comprises steps of arranging an ultrasonic probe around an outer circumferential surface of a first pipe member of the metallic pipe being bonded together by diffusion bonding, and measuring reciprocating time, by said ultrasonic probe, for an ultrasonic wave incident perpendicularly toward the outer circumferential surface of said pipe member to reflect back its echo therefrom, arranging an ultrasonic probe around an outer circumferential surface of a second pipe member of the metallic pipe, and measuring reciprocating time, by the ultrasonic probe, for an ultrasonic wave incident perpendicularly in the same direction as that of the first pipe member to the outer circumferential surface of said second pipe member to reflect back its echo therefrom, and calculating a size of a step fault produced at a bonding portion along the outer circumferential surface based on the reciprocating time of the outer reflected echo measured in said measurements.

It is an effect of the method for evaluating bonding properties of a metallic pipe of the second invention, that a size of the outer step fault can be measured accurately and efficiently even if the accuracy or a flatness of the pipe members are poor.

In addition, a third invention of the present patent application in regard to the method for evaluating bonding properties of a metallic pipe, the method comprises steps of measuring reciprocating time for an ultrasonic wave incident vertically to an outer circumferential surface of a first pipe member of the metallic pipe being bonded together by diffusion bonding to reflect back its echo from the outer circumferential surface and from an inner circumferential surface of said first pipe member of the metallic pipe, measuring reciprocating time for an ultrasonic wave incident vertically to an outer circumferential surface of a second member of said metallic pipe to reflect back its echo from the outer circumferential surface and from an inner circumferential surface of said second pipe member of the metallic pipe, and calculating a size of a step fault produced along the inner circumferential surface of a bonding portion from the reciprocating time of the outer reflected echo and the inner reflected echo measured in said measurements.

It is an effect of the third invention that a size of the inner step fault can be measured accurately and efficiently even in the case where the size accuracy or a degree of flatness of the pipe members is poor.

In this case, the reciprocating time of the outer reflected echo and the reciprocating time of the inner reflected echo may be measured in a vicinity of said bonding portion in each of said measurements. Otherwise, the reciprocating time of the outer reflected echo may be measured in a vicinity of the bonding portion and the reciprocating time of the inner reflected echo may be measured in a heat-unaffected portion in each of said measurements. Further, it is possible to provide an additional step of calculating a thickness of said bonding portion from the reciprocating time of the outer reflected echo and the reciprocating time of the inner reflected echo measured in each of said measurements.

With the foregoing, since an ultrasonic wave is made enter from an ultrasonic probe arranged outside the metallic pipe bonded together by diffusion bonding toward each of the pipe members perpendicularly in the same direction, it is possible to calculate respective distances between the outer circumferential surfaces of the metallic pipes and the ultrasonic probe in reference to the reciprocating time of the outer reflected echo. Further, it is possible to calculate the wall thickness of each of the metallic pipes based on the difference between the reciprocating time of the outer reflected echo and the reciprocating time of the inner reflected echo measured for on the pipe members.

Accordingly, it is possible to perform an accurate and efficient calculation of a size of step faults produced at the outer circumferential surface and/or the inner circumferential surface of the bonding portion even if the size accuracy or a degree of the flatness of pipe members are poor. To obtain the size of step faults, the reciprocating time of the outer reflected echo and the reciprocating time of the inner reflected echo are measured on each of the two metallic pipes being adjacent to each other through the bonding portion under the condition where the predetermined relation is kept between the ultrasonic probe and the metallic pipe.

In addition, in the case where the reciprocating time of each of the outer reflected echoes and the reciprocating time of each of the inner reflected echoes are measured in the vicinity of the bonding portion, necessary data to calculate the sizes of the outer step fault and the inner step fault and the thickness of the bonding portion may be obtained in a smaller number of times of measurements thereby improving the efficiency of the measurement.

In addition, in the case of measuring the reciprocating time of the outer reflected echoes is received in the vicinity of the bonding portion and that of the inner reflected echoes in a heat-unaffected portion, the effect is that a measurement error of the reciprocating time of the inner reflected echo caused by a variation in structure or in elastic modules due to the heat during bonding operation is restricted, and thereby improving accuracy in measuring the size of the step fault and the thickness of the bonding portion.

Further, if there is provided a step for calculating the thickness of the bonding portion based on the reciprocating time for both the outer reflected echoes and the inner reflected echoes, it is possible to estimate an area of the bonding portion. With the foregoing, it is possible to estimate the strength of the bonded body in a non-destructive manner.

As described above, in accordance with the method for evaluating bonding properties of a metallic pipe of the present invention, the size of the outer step fault, which conventionally requires a tremendous amount of labor and the size of the inner step fault, which is conventionally difficult to measure, can be measured with highly accuracy and efficiency. Thus, through application of this method of the present invention, for example, to evaluate quality of an oil well pipe or a piping a chemical plant, the reliability of bonding operation can be remarkably improved. As described above, this invention has a great effect in industry.

The method for evaluating bonding properties of a metallic pipe, in accordance with a fourth invention of the present patent application comprises a step of measuring, in advance of a pipe expansion operation, at least one selected from a degree of shape discontinuity, a degree of defect at a bonding portion, and a degree of change in crystal structure, and comparing a measurement value with a predetermined threshold value to evaluate suitability of the bonding properties for applying pipe expansion.

In this case, "the shape discontinuity of the bonding portion" of the metallic pipe may include a step fault on the inner and/or outer circumferential surface of the bonding portion. The causes of the step fault include a minute difference in an outer diameter or an inner diameter of the adjoining pipe or misalignment of the axes of the pipe members at the bonding interface or the like. The shape discontinuity also includes step faults produced by the bonding material being squeezed out and solidified at the bonded surface upon binding the metallic bonded pipes or the like by the liquid phase diffusion bonding method.

Further, "the defect at the bonding portion" includes, shape defects such as a crack or a void, or defects of metallic structure such as a poor diffusion of bonding material to the base material. In addition, "the change in the crystal structure at the bonding portion" includes growth of the grain particles due to an excessive heating or the minute grain particles due to an excessively low heating temperature or insufficient heating during the diffusion bonding operation.

In accordance with the method for evaluating bonding properties of a metallic pipe of the fourth invention, suitability for applying an pipe expansion operation is evaluated to see, in advance of pipe expansion operation, if the bonding portion can be expanded safely. This eliminates the possibility of such troubles, at the site of pipe expansion, including a crack produced at the bonding portion or separation of the metallic pipe at the bonding portion, resulting that such metallic pipes can no longer be used. Thus, extra work for replacing the defected pipes with another pipe or for repairing such pipes can be eliminated. As the result, labor effectiveness, for example in plant assembly, can be improved, and a tremendous amount of cost required for repairing work can be reduced.

In order to eliminate such bonding deficiency as described above, the method for evaluating bonding properties of a metallic pipe comprises a first step of measuring said bonding portion of said metallic pipe for the degree of the shape discontinuity, a second step of measuring said bonding portion for the degree of the defect, and a third step of measuring bonding portion and its nearby portion for the degree of change in the crystal structure and the fist step is carried out prior to the other steps.

In this case, as the measurement method to carry out the first step, in addition to the ultrasonic measurement, the method disclosed in the Japanese Patent Application No. Hei 11 (1999) - 181638 (not yet published) by the present applicant may be applied. In the method, an outer diameter size and a wall thickness of the pipe members to be bonded together are preliminary measured. An inner diameter step fault size is calculated by measuring an outer diameter step fault size after bonding operation. As the second step and its measurement method, in which the defect at the bonding portion or variation of crystal structure needs to be measured, the ultrasonic measurement is desirable.

Then, in the case where the ultrasonic measurement is applied for the first step, such metallic pipes having "the discontinuity in shape at the bonding portion" are excluded through this measurement. As the result, the number of the metallic pipes need to be measured by the ultrasonic measurement in the second step and in the third step is decreased. Accordingly, redundancy in the ultrasonic measurement is eliminated and thus the efficiency in measurement can be increased in that the measuring time is shortened.

In the case, the metallic pipes having a shape discontinuity at the bonding portion (such as presence of a step fault or a material being squeezed-out and solidified) are excluded by the ultrasonic measurement. In addition, the metallic pipes having a defect at the bonding portion (a defect in shape such as a crack or a void, or a defect in metallic structure due to inferior diffusion of bonding material into the base material) are excluded as well as the pipe having a defect in crystal structure at the bonding portion (the grain particles changed into rough large size or insufficient bonding due to minute grain particles cased by a low heating temperature). As the result, insufficiently in the pipe expansion operation at the site is completely eliminated thereby assuring quality of the pipe expansion operation.

The fourth invention can be suitably applied to the metallic pipe bonded by various methods including the welding method (orbital welding method), the friction method and a diffusion bonding method. Yet, the forth invention is most suitably applied to the metallic pipes bonded together by the diffusion bonding method, particularly by the liquid phase diffusion bonding method. The metallic pipes bonded together by the liquid phase diffusion bonding method are superior in view of bonding properties such as bonding strength, an air-tightness and an pressure-tightness or the like. Thus, these pipes are preferably applied in a pipe line or an oil well pipe and the like.

In the fourth invention, the measurement of a degree of "discontinuity in shape of the metallic pipe bonding portion" is preferably carried out with the use of an ultrasonic wave. The ultrasonic wave is made enter perpendicularly to the outer surface the metallic pipes in the vicinity of the bonding portion. The evaluation is made based on the difference in detection time of the reflected echo at the outer surface and a reflected echo from the inner surface of each of the metallic pipes. This result in an advantage that an accurate evaluation can be attained.

Further, it is preferable that the measurement of a degree of "defect at the metallic pipe bonding portion" is carried out with the use of an ultrasonic wave. The ultrasonic wave is made enter from both sides of the bonding interface or from one of the sides, the evaluation is made based on the size of the ultrasonic wave echo reflected at the defect present at the bonding interface. With such an arrangement as above, the size of the detected ultrasonic wave echo clearly indicates presence of the defect or its degree, so that it has an advantage that an accurate evaluation result can be attained.

Further, it is preferable that the measurement of a degree of variation of "crystal structure of the bonding portion of the metallic pipe" is carried with the use of an ultrasonic wave. The ultrasonic wave is made enter from the both sides of the bonding interface or from one of the sides and evaluating is made based on the size of the ultrasonic wave echo which passes through the bonding interface. With such an arrangement as above, if there is a bonding deficiency caused by inferior heating, it is clearly indicated by the size of the propagated echo heights of the ultrasonic wave. This results in the advantage that an accurate evaluation result can also be attained.

Through various kinds of ultrasonic measurements on binding properties of the metallic pipes , metallic pipes which may cause bonding defectives upon the pipe expansion operation are excluded in advance. As the result, occurrences of deficiencies such as a crack at the bonding portion or on the surface of the pipe, or a separation of the bonding portion, upon the pipe expansion operation are eliminated. As the result, the efficiency in the pipe expansion operation is significantly improved.

BRIEF DESCRIPTION OF THE DRAWINGS

FIG. 22 is a view illustrating a process to exclude a defective product the evaluation illustrated in FIG. 21. In this figure, the mark of ● indicates a test material in which a crack is produced at the bonding portion, and the mark of ○ indicates a test material without a crack produced at the bonding portion, during a pipe expansion operation.

DETAILED DESCRIPTION OF THE PREFERRED EMBODIMENTS

A detailed description of various kinds of preferred embodiments of a method for evaluating bonding properties of a metallic pipe embodying the present invention will now be given referring to the accompanying drawings.

First Preferred Embodiment

Figure 1:
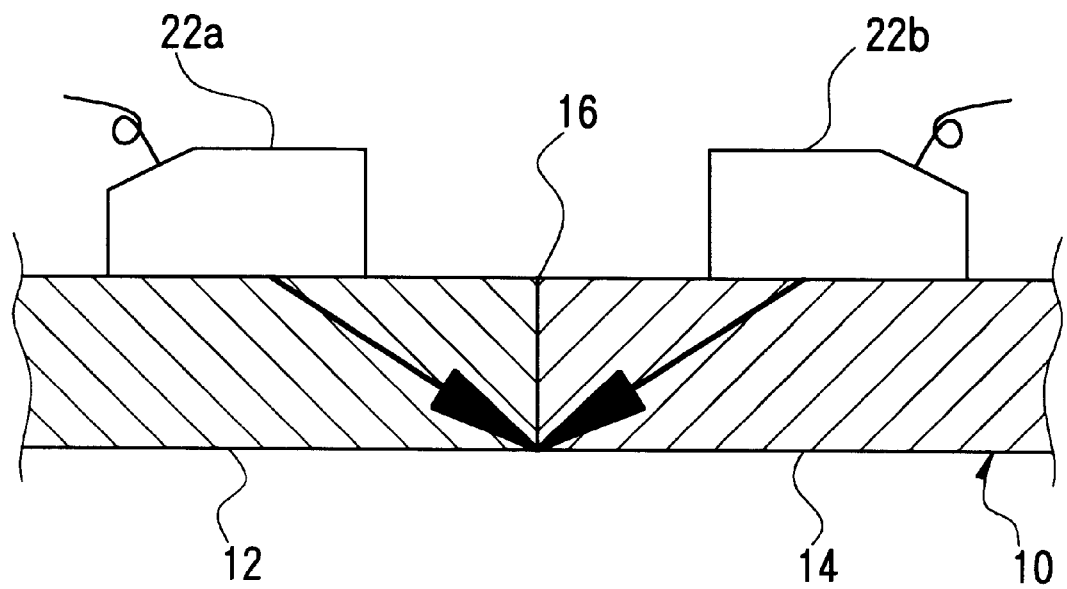
FIG. 1 is a schematic configuration view for showing a method for evaluating quality of a metallic bonded pipe of the present invention.

FIG. 1 is a schematic view showing one example of a method for examining a bonding portion of a first preferred embodiment of the present invention. In FIG. 1, a metallic bonded pipe (a bonded body) 10 is made such that the metallic pipes 12 and 14 are bonded together in diffusion through a bonding interface 16. In addition, probes 22a and 22b are arranged on outer circumferential surfaces of the metallic pipes 12 and 14 respectively.

In this case, material and size of the metallic pipes 12, 14 constituting the bonded body 10 are not particularly restricted. In addition, the metallic pipes 12, 14 may be electrical seam welded pipes or seamless steel pipes. Although the present invention is particularly preferable as a method for examine a step fault and a defect produced at the inner circumferential surface of the bonded body 10 made by bonding the metallic pipes 12 and 14 together, it goes without saying that the method is applicable for examining a step fault and a defect produced at an edge of the bonding interface of a plate-like bonded body.

As a diffusion boning method, there are provided a solid phase diffusion boning method and a liquid phase diffusion bonding method. In the solid phase diffusion boning method, two metallic pipes are abutted directly to each other and elements are diffused while keeping a solid phase therebetween. In the liquid phase diffusion bonding method, an insert material is inserted into the bonding interface between the two metallic pipes, and then the insert material is melted to diffuse part of elements at the metallic pipe. In the present invention, both the solid phase diffusion bonding method and the liquid phase diffusion bonding method can be applied as the method for bonding to make the bonded body 10.

Figure 2:
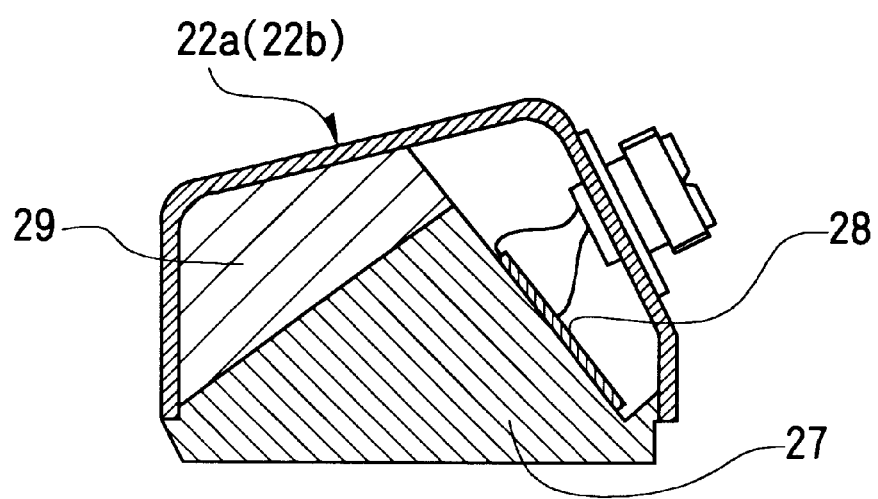
FIG. 2 is a sectional view for showing a slant probe used in the present invention.

As shown in FIG. 2, as the probes 22a and also as the probe 22b, a so-called slant angle probe is used in which a vibrator 28 is adhered to a wedge 27 made of synthetic resin such as acrylic resin. An incident angle of the slant angle probe may be appropriately determined in accordance with a shape, a size and the like of the bonded body 10.

As conventionally known, the vibrator 28 is constructed such that electrodes are adhered to both surfaces of a thin plate made of piezoelectric material such as crystal, niobate and zircon titanate or the like. A sound absorbing material 29 is adhered to the wedge 27 so as to absorb an ultrasonic wave undesirably reflected at the contact surface between the probe 22a and the metallic tube 12, or at the contact surface between the probe 22b and the metallic pipe 14. Further, the bottom surfaces of the probes 22a, 22b are made to be curved surfaces in compliance with curvatures of the metallic pipes 12, 14 so as to make absolute contact therebetween.

In addition, a coupling medium needs to be arranged to fill in the clearances between the probes 22a, 22b and the metallic pipes 12, 14. It is because presence of clearances between the probes 22a, 22b and the metallic pipes 12, 14, hinder effective transmission and receiving of the ultrasonic wave. Here, the coupling medium may be any medium enabling efficient transmission of ultrasonic wave to be performed, and therefore, various kinds of coupling media may be selectively used as required. Examples of the contact media are water, oil and glycerol.

Described hereinafter is one exemplary method, in accordance with the method for evaluating the bonding properties of the bonded portion of the present invention, for examining presence of a step fault and a defect at the edge of the bonding interface 16 as well as its size. The method for examining the bonded portion in accordance with the present invention comprises a first measuring step, a second measuring step, a step fault discriminating step and a defect discriminating step.

First, the first measuring step will be described. The first measuring step is a step in which the probe 22a is arranged on the outer circumferential surface of one metallic pipe constituting the bonded body 10, for example the metallic pipe 12 as shown in FIG. 1, an ultrasonic wave is incident from the probe 22a toward the edge of the bonding interface 16 and the reflected echo height of the ultrasonic wave reflected from the edge of the bonding interface 16 is measured.

To be more specific, the reflected echo height is measured by following the procedure described hereinafter. First, a high frequency pulse generated by a not shown synchronous control section is sent to the probe 22a via a not shown high frequency cable. As the high frequency pulse sent to the probe 22a is applied to the electrodes adhered to the both surfaces of the vibrator 28, the vibrator 28 is extended in a direction of its thickness so as to generate an ultrasonic wave.

The generated ultrasonic wave passes through the wedge 27 and enters into the metallic pipe 12 and then reaches the edge of the bonding interface 16. At this time, if there is a step fault and/or a defect present at the edge of the bonding interface 16, the ultrasonic wave is reflected by the step fault and/or defect.

Thereafter, the ultrasonic wave reflected at the edge of the bonding interface 16 goes back through the substantially same path as that of the incident wave and is received by the probe 22a. The received ultrasonic wave is transmitted to the vibrator 28 installed at the probe 22a to cause the vibrator 28 to be extended or retracted in a direction of its thickness. Then, the thus generated mechanical vibrations are further converted into electrical signals by the vibrator 28 and sent to a receiving section of a not shown inspection device through the high frequency cable. Then, by measuring a value of electrical energy received at the probe 22a, the reflected echo height of the reflected ultrasonic wave is measured.

Next, the second measuring step will be described as follows. The second measuring step is a step in which the probe 22b is arranged on the outer circumferential surface of the other metallic pipe constituting the bonded body 10, the metallic pipe 14 in this case to measure the reflected echo height of the ultrasonic wave reflected from the edge of the bonding interface 16 with the use of the probe 22b. The procedure of measuring the reflected echo height in the second measuring step is substantially the same as that of the first measuring step, except that the ultrasonic wave is incident in a direction opposite to that of the first measuring step.

In the aforesaid example, a so-called one probe slant angled defect evaluating method in which transmission and receiving of the ultrasonic wave are carried out with one probe. However, the method for measuring the reflected echo height is not limited to this method.

For example, it is also possible to arrange two slant angled probes on one metallic pipe (for example, the metallic pipe 12). The ultrasonic wave is made enter from one of the slant angled probe toward the edge of the bonding interface 16 and the ultrasonic wave reflected therefrom is received at the other slant angled probe. In this case, the two slant angled probes may be arranged in a vertical orientation against the bonding interface 16 and on the linear line, or instead, they may be arranged at a predetermined angle against the bonding interface 16.

Further, if a step fault and a defect produced at the edge of the bonding interface 16 are small in size, it is satisfactory to merely provide a direct incidence of the ultrasonic wave toward the edge of the bonding interface 16. On the other hand, if a step fault and/or a defect is large in size, it is desirable to cause the two slant angled probes to scan in a vertical direction relative to the bonding interface 16 while keeping a specified distance between the probes. In addition, if one or two or more probes arranged on one metallic pipe scan in parallel relative to the bonding interface 16, an entire circumference of the edge of the bonding interface 16 can be examined.

Further, it is also applicable that the first measuring step and the second measuring step are carried out with the use of one probe, or with the use of the two probes 22a, 22b arranged at both sides of the bonding interface 16, as shown in FIG. 1, to measure the reflection echo height.

However, in the case where the two probes 22a, 22b are arranged at both sides of the bonding interface 16, and the reflection echo height is measured with the use of these probes, it is necessary to adjust a timing of generating a pulse, a refraction angle, and the like in such a manner that ultrasonic wave transmitted from one probe (for example, the probe 22a) may not be received by the other probe (in this case, the probe 22b).

Next, the step fault discriminating step will be described hereinafter. The step fault discriminating step is to calculate a difference between the reflected echo heights measured in the first measuring step and in the second measuring step respectively. As later described, the difference in the reflected echo heights between each measurement corresponds to a size of the step fault, and therefore, through calculation of the difference in the reflected echo heights, presence of a step fault at the edge of the bonding interface 16, a projecting direction of the step fault along with its size can be discriminated.

Described hereinafter is the defect discrimination step. The defect discriminating step is a step to calculate a minimum value of the reflected echo height measured in the first measuring step and the second measuring step respectively. As later described, the minimum value of the reflected echo height corresponds to a size of the defect, ant therefore, through comparison of the minimum value of the reflected echo height with a noise echo level, presence of a defect at the edge of the bonding interface 16 along with its size can be discriminated.

Next, there will be described a principle for discriminating presence of a step fault and a defect, along with their sizes, at the edge of the bonding interface 16, in particular, at the inner circumferential surface by the method for evaluating bonding properties of the present invention.

Figure 3A:
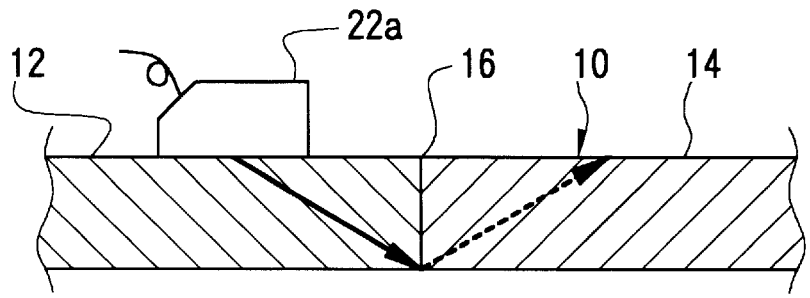
FIGS. 3A and 3B are illustrative views for showing a state of reflection of an ultrasonic wave in the case where an edge of a bonding interface has no step fault and no defect.

Described first is the case where no step fault and no defect are present at the edge of the bonding interface. First, in the first measuring step, as shown in FIG. 3A, an ultrasonic wave is made enter from the probe 22a arranged on the metallic pipe 12 toward the edge of the inner circumferential surface of the bonding interface 16. In this case, since the bonding interface 16 has neither a step fault nor a defect, the incident ultrasonic wave is reflected at the inner circumferential surface of the bonded body 10 and transferred directly toward the metallic pipe 14. Therefore, in the first measuring step, the reflected echo height merely within a noise echo level is measured.

Figure 3B:
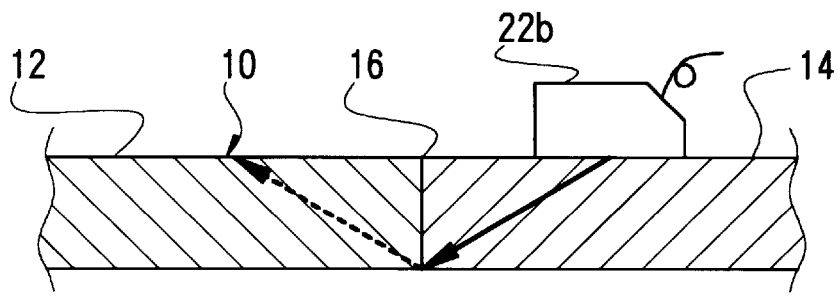

Also in the second measuring step, as shown in FIG. 3B, an ultrasonic wave is made enter from the probe 22b arranged on the metallic pipe 14 toward the edge of the inner circumferential surface of the bonding interface 16. In this case, similarly to the first measuring step, since the incident ultrasonic wave is reflected at the inner circumferential surface of the bonded body 10 and transferred directly toward the metallic pipe 12, the reflected echo height merely within a noise echo level is measured also in the second measuring step.

Figure 7:
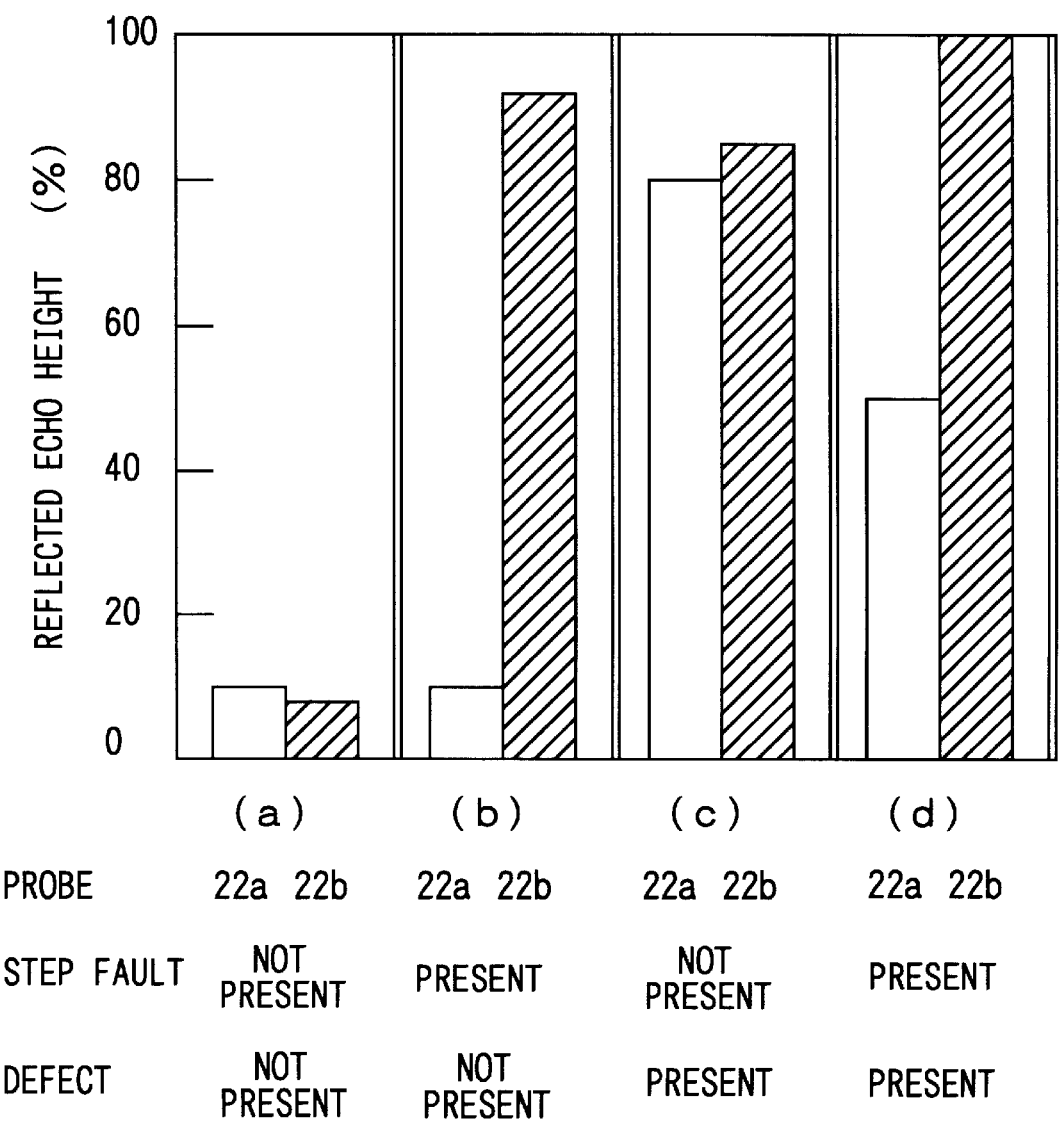
FIG. 7 is a view for showing a reflected echo height measured in reference to FIGS. 3 to 6.

Accordingly, as shown in FIG. 7(a), in the case where there is no difference in the reflected echo heights detected between the first measuring step and the second measuring step, and the reflected echo heights are within a noise echo level, it is easily judged that the bonding interface 16 has no step fault and no defect.

Figure 4A:
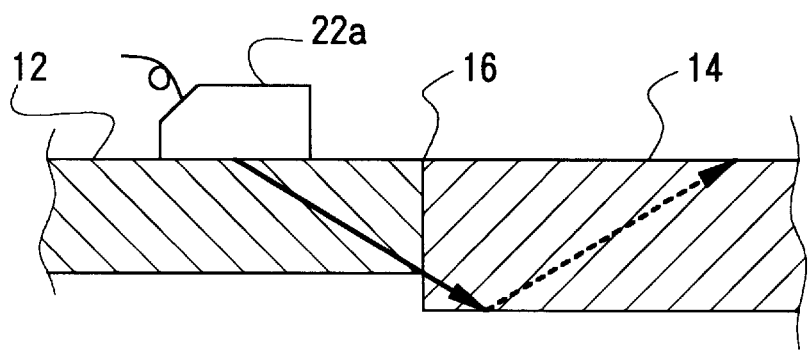
FIGS. 4A and 4B are illustrative views for showing a state of reflection of an ultrasonic wave in the case where only a step fault is present at an edge of a bonding interface.

Described next is the case where only the step fault is present at the edge of the bonding interface, and the metallic pipe 14 is protruded toward the center. First, in the first measuring step, an ultrasonic wave is made enter from the probe 22a arranged on the metallic pipe 12 toward the edge of the inner circumferential surface of the bonding interface 16 as shown in FIG. 4A. In this case, the metallic pipe 14 is protruded more than the metallic pipe 12, the incident ultrasonic wave passes through the bonding interface 16 and is transferred toward the metallic pipe 14 without being reflected. Thus, only the reflected echo height within a noise echo level is measured in the first measuring step,.

Figure 4B:
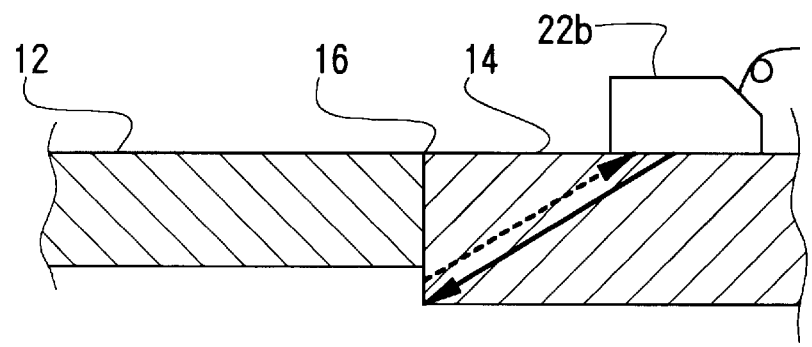

On the other hand, in the second measuring step since the metallic pipe 14 is protruded more than the metallic pipe 12, an ultrasonic wave is made enter from the probe 22b arranged on the metallic pipe 14 is reflected at the step fault at the bonding interface 16, and the reflected ultrasonic wave is received by the probe 22b as shown in FIG. 4B. As the result, the reflected echo height exceeding a noise echo level is measured in the second measuring step.

Accordingly, as shown in FIG. 7(b), if a difference is present between reflected echo heights detected in the first measuring step and in the second measured step, and either one of them is within a noise echo level, it is easily judged that only a step fault is present at the bonding interface 16.

In addition, which of the metallic pipes is protruded toward the center may be determined in the following way. First, either one of the metallic pipes, the metallic pipe 12, for example, is determined as a standard. Next, difference in reflected echo height calculated by subtracting the reflected echo height ($V_3$) measured on the metallic pipe 14 from reflected echo height ($V_2$) measured on the metallic pipe 12 being the standard pipe ($\Delta V = V_2 - V_3$). Referring to the sign of the thus calculated difference, the protruded pipe is easily determined.

In the case of the example shown in FIGS. 4A and 4B, since the difference Δ V of the reflected echo height is a negative value. It indicates that the metallic pipe 14 is protruded toward center more than that of the metallic pipe 12. On the other hand, if the difference Δ V of the reflected echo height is a positive value, different from the example shown in the FIGS. 4A and 4B, it indicates that the metallic pipe 12 is protruded toward the center more than the metallic pipe 14.

The reflected echo height becomes higher in proportional to a step fault. Accordingly, if a relation between a size of the step fault and a reflected echo height is previously obtained under the same condition as that of the actual bonded body, it is possible to predict a size of the step fault from the absolute value of a reflected echo height measured on to the actual bonded body with high accuracy.

Figure 5A:
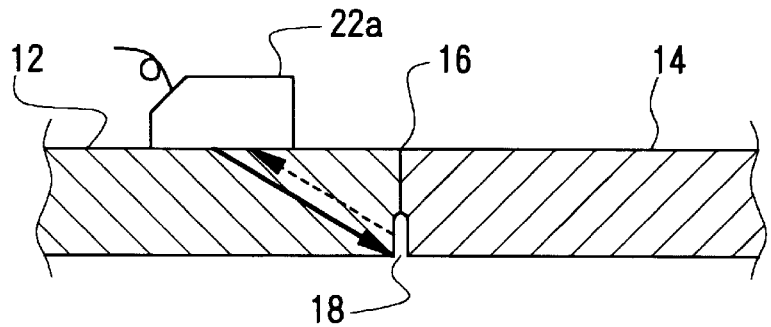
FIGS. 5A and 5B are illustrative views for showing a state of reflection of an ultrasonic wave in the case where only a defect is present at an edge of a bonding interface.

Next, there will be described the case where only the defect is present at the edge of the bonding interface. First of all, an ultrasonic wave is made enter from the probe 22a arranged on the metallic pipe 12 toward the edge of the inner circumferential surface of the bonding interface 16 in the first measuring step as shown in FIG. 5A. In this case, since the defect 18 is present at the edge of the inner circumferential surface of the bonding interface 16, the incident ultrasonic wave is reflected at the defect 18 and the reflected ultrasonic wave is received by the probe 22a. Thus, the reflected echo height exceeding the noise echo level is measured in the first measuring step.

Figure 5B:
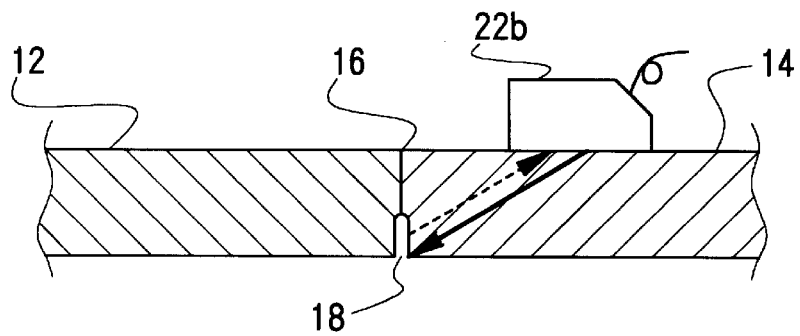

In addition, when an ultrasonic wave is made enter from the probe 22b arranged on the metallic pipe 14 toward the edge of the inner circumferential surface of the bonding interface 16 in the second measuring step, the incident ultrasonic wave is reflected at the defect 18 as shown in FIG. 5B, and the reflected ultrasonic wave is received by the probe 22b. Thus, the reflected echo height exceeding the noise echo level is measured also in the second measuring step.

Accordingly, as shown in FIG. 7(c), if there is no difference in the reflected echo heights measured in the first measuring step and the second measuring step, and both of the reflected echo heights exceed the noise echo level, it is easily judged that only the defect is present at the bonding interface 16.

The reflected echo height becomes higher in proportional to an area of a defect. Accordingly, if a relation between a size of the defect and a reflected echo height is previously obtained under the same condition as that of the actual bonded body, it is possible to predict a size of the defect from a reflected echo height measured on the actual bonded body with high accuracy.

Figure 6A:
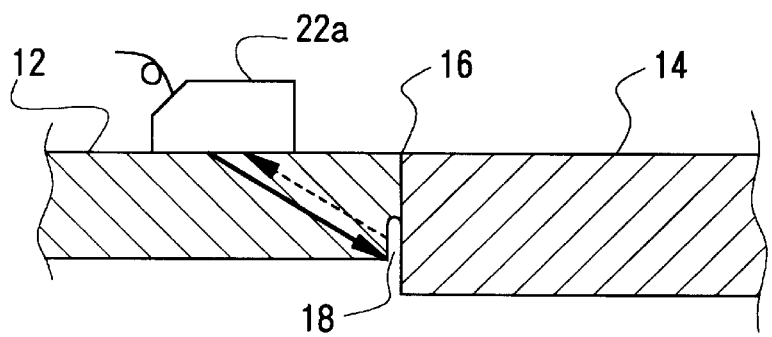
FIGS. 6A and 6B are illustrative views for showing a state of reflection of an ultrasonic wave in the case where both a step fault and a defect are present at an edge of a bonding interface.

Described next is the case where both a step fault and a defect are produced at the edge of the bonding interface, and where the metallic pipe 14 is protruded toward the center more than the metallic pipe 12. First, in the first measuring step, an ultrasonic wave is made incident from the probe 22a arranged on the metallic pipe 12 toward the edge of the inner circumferential surface of the bonding interface 16, as shown in FIG. 6A.

In this case, since there is a defect at the edge of the bonding interface 16, and the metallic pipe 14 is protruded toward the center more than the metallic pipe 12, the incident ultrasonic wave is reflected back at the defect 18, and the reflected ultrasonic wave is received by the probe 22a. Thus, only the reflected echo height from the defect 18 is measured in the first measuring step.

Figure 6B:
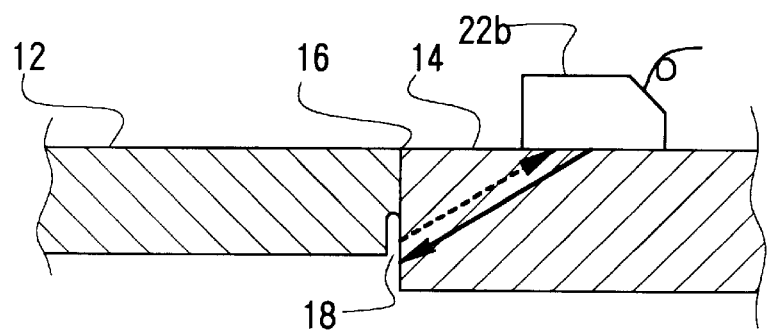

In the second measuring step, on the other hand, when an ultrasonic wave is made enter from the probe 22b arranged on the metallic pipe 14 toward the edge of the inner circumferential surface of the bonding interface 16, the incident ultrasonic wave is reflected at both the step fault and the defect 18, as shown in FIG. 6B, and the reflected ultrasonic wave is received by the probe 22b. Thus, the reflected echo heights from both the step fault and the defect 18 are measured in the second measuring step.

Accordingly, as shown in FIG. 7(d), in the case where there is a difference in the reflected echo heights detected in the first measuring step and the second measuring step, and both of the reflected echo heights exceed the noise echo level, it is easily judged that both step fault and defect are present at the bonding interface 16.

Further, it is apparent that the difference Δ V between the reflected echo heights measured in the first measuring step and in the second measuring step corresponds only to a size of the step fault, while minimum values of the reflected echo heights correspond only to the defect 18. That is to say, even in the case where both defect and step fault are present, it is still possible to detect presence of a step fault and a defect as well as to measure their size with high accuracy in a non-destructive manner.

First Example

Description is now made to an example of application of the method of the present invention to evaluate bonding properties of a bonded body comprising carbon steel pipes bonded together by the liquid phase diffusion bonding method.

As metallic pipes used for the bonded body, carbon steel pipes for machine structure, STKM 12B (JIS G3445) having an outer diameter of 140 mm and a wall thickness of 7 mm was used. The two carbon steel pipes were abutted against each other with an intervention of a Ni system alloy foil having a thickness of 40 μm therebetween, and then the liquid phase diffusion bonding was carried out in an Ar atmosphere with a bonding temperature of 1300° C., holding time of 60 seconds and pressing force of 3.0 MPa.

Then, measurement was carried out on the thus obtained bonded body, as shown in FIG. 1, to obtain the difference in the echo height. First, the slant angled probe 22a was arranged on the metallic pipe 12 and the reflected echo height $V_2$ was measured (the first measuring step). Then, the slant angled probe 22b was arranged on the metallic pipe 14 and the reflected echo height $V_3$ of the ultrasonic wave was measured (the second measuring step). Thereafter, the difference in the reflected echo height Δ V was calculated from the reflected echo heights $V_2$, $V_3$ measured respectively in the first measuring step and the second measuring step.

Here, as a ultrasonic defector, USD15 (manufactured by Krautkramer Japan Co., Ltd.) was used. Used as the probes 22a, 22b were the slant angled probes with a refraction angle of 70° and a nominal frequency of 5 MHz having an oscillator of a 5 mm×5 mm square comprised from zircon titanate.

After measuring the reflected echo height, each of the bonded bodies was cut to measure a size $L_g$ (mm) of the step fault and a size $L_f$ (mm) of the defect produced at the inner circumferential surface of the bonding interface. Table 1 shows the attained results. Table 1, indicates that, when the size $L_g$ (mm) of the step fault is a positive value, the metallic pipe 12 being a reference pipe is protruded toward the center, and when the size $L_g$ (mm) of the step fault is a negative value, the metallic pipe 14 is protruded toward the center.

TABLE 1

| Test No. | Reflected Echo Height (db) | | | Step Fault Lg (mm) | Defect Lf (mm) |
|---|---|---|---|---|---|
| | V2 | V3 | ΔV = V2 − V3 | | |
| 1 | −85 | −85 | 0 | 0.0 | 0.0 |
| 2 | −82 | −58 | −24 | −2.2 | 0.0 |
| 3 | −80 | −66 | −14 | −1.2 | 0.0 |
| 4 | −82 | −76 | −6 | −0.4 | 0.0 |
| 5 | −77 | −84 | 7 | 0.5 | 0.0 |
| 6 | −71 | −84 | 13 | 1.0 | 0.0 |
| 7 | −63 | −83 | 20 | 1.8 | 0.0 |
| 8 | −76 | −77 | 1 | 0.0 | 0.6 |
| 9 | −69 | −67 | −2 | 0.0 | 1.4 |
| 10 | −65 | −65 | 0 | 0.0 | 1.8 |
| 11 | −59 | −60 | 1 | 0.0 | 2.5 |
| 12 | −76 | −70 | −6 | −0.5 | 0.6 |
| 13 | −69 | −57 | −12 | −1.1 | 1.4 |
| 14 | −68 | −75 | 7 | 0.4 | 0.8 |
| 15 | −58 | −70 | 12 | 1.2 | 1.2 |

In the case of the bonded body having neither a step fault nor a defect, the reflected echo height measured in the first measuring step and the reflected echo height measured in the second measuring step were within a noise echo level (a test No. 1), while in the case of the bonded body having a step fault, one of the reflected echo height exceeded a noise echo level (test Nos. 2 to 7).

In addition, in the case where the metallic pipe 12 being a reference pipe was protruded more than the metallic pipe 14, the difference Δ V between the reflected echo heights was a positive value (test Nos. 5 to 7), while in the case where the metallic pipe 14 was protruded more than the metallic pipe 12, the difference Δ V between the reflected echo heights was a negative value (test Nos. 2 to 4).

On the other hand, in the case where only a defect was present on the bonded body, there was no difference in the reflected echo heights between the two measurement, and both exceeded a noise echo level (test Nos. 8 to 11). In the case where both a step fault and a defect were present on the bonded body, there was a difference in the reflected echo height between the two measurement and both exceeded a noise echo level (test Nos. 12 to 15).

Accordingly, the foregoing results clearly show that presence of a step fault and a defect can be easily determined based on a difference between a reflected echo heights measured on the metallic pipe 12 and a reflected echo height measured on the other metallic pipe 14. In addition, in the case where a step fault is present, the sign of the value indicating the difference between the reflected echo height allows to determine which of the metallic pipes is protruded than the other.

Figure 8:
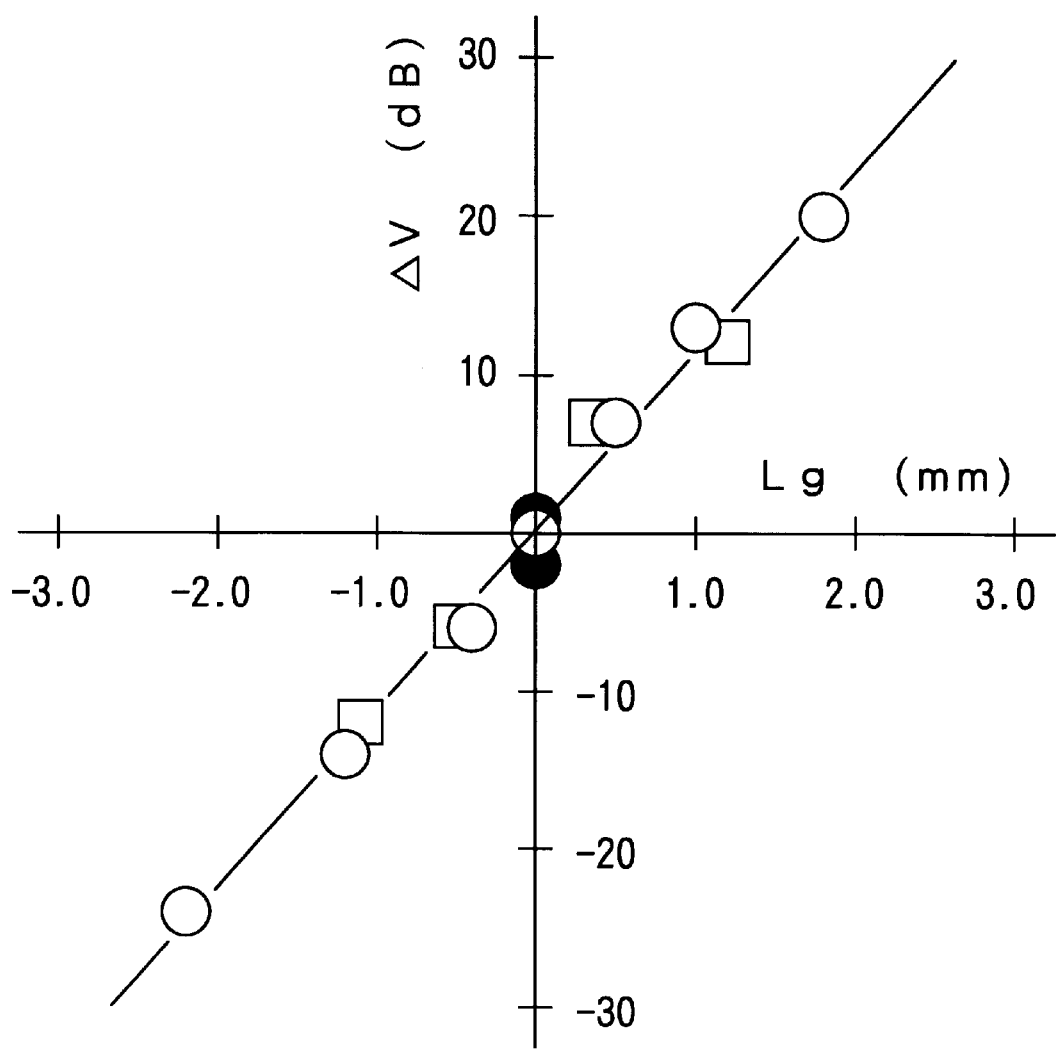
FIG. 8 is a view for showing a relation between a difference $\Delta V$ (dB) in a reflected echo height and a size of step fault $L_g$ (mm) present at the edge of the bonding interface.

FIG. 8 shows a relation between a difference Δ V (dB) in the reflected echo height and a size $L_g$ (mm) of the step fault. In FIG. 8, the mark ○ indicates a difference Δ V of the reflected echo of the bonded body having only a step fault, and the mark ● indicates a difference Δ V between the reflected echo heights of the bonded body having only the defect. Further, the mark □ indicates a difference Δ V of the reflected echo height in the bonded body having both a step fault and a defect.

As is apparent from FIG. 8, the data (●) on the bonded body having only a defect are concentrated near the origin with the difference Δ V between the reflected echo heights are approximately 0. From FIG. 8, it is also apparent that not only the data (○) on the bonded body having only a step fault but also the data (□) on the bonded body having both a step fault and a defect appear substantially linearly. This indicates that there is a strong relation between the difference Δ V between the reflected echo heights and the size $L_g$ of the step fault.

That is to say, not only in the case where only a step fault is present at the edge of the bonding interface, but also in the case where both a step fault and a defect are present, through measuring the difference Δ V between the reflected echo heights, the size $L_g$ of the step fault can be accurately detected.

Figure 9:
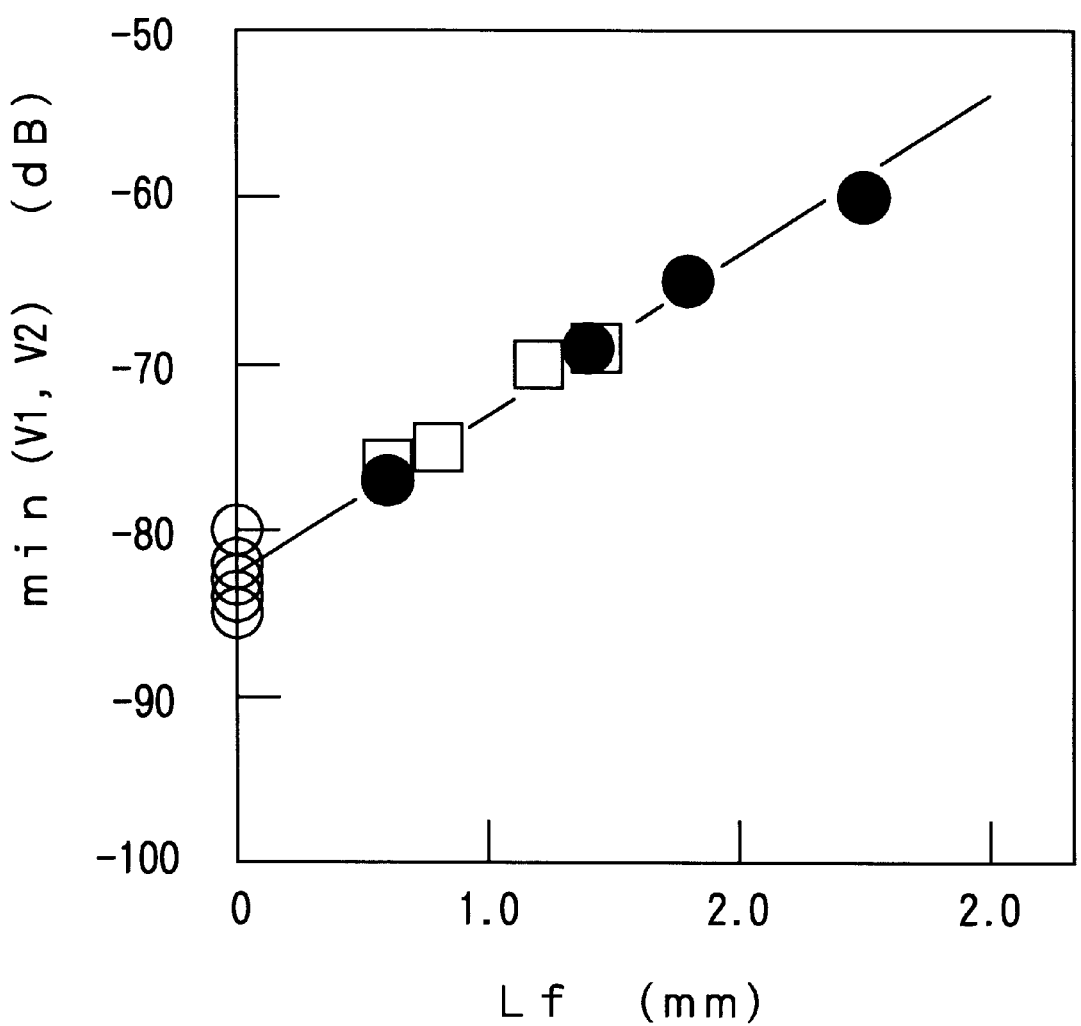
FIG. 9 is a view for showing a relation between a minimum values $\min(V_1, V_2)$ (dB) of a reflected echo height and a size $L_f$ (mm) of a defect present at the edge of the bonding interface.

FIG. 9 shows the relation between the minimum values min ($V_1$, $V_2$) in the reflected echo height and the size $L_f$ (mm) of the defect. In FIG. 9, the mark ● indicates the minimum values min ($V_1$, $V_2$) in the reflected echo heights in the case where only a defect is present and the mark □ indicates minimum values min ($V_1$, $V_2$) in the reflected echo heights in the case where both a step fault and a defect are present. Further, the mark ○ indicates minimum values min ($V_1$, $V_2$) in the reflected echo heights in the case where only a step fault is present.

It is apparent from FIG. 9 that the data (○) on the bonded body having only a step fault concentrates around −85 dB or so, with the minimum values min ($V_1$, $V_2$) of the reflected echo height being approximately equal to a noise level echo. From FIG. 9, it is also apparent that not only the data (●) on the bonded body having only the defect, but also the data (□) on the bonded body having both a step fault and a defect appear substantially linearly. This indicates that there is a strong relation between the minimum values min ($V_1$, $V_2$) of the reflected echo heights and the size $L_f$(mm) of the defect.

That is to say, not only in the case where only a defect is present at the edge of the bonding interface, but also in the case where both a defect and a step fault are present, through measuring the minimum values min ($V_1$, $V_2$) of the reflected echo heights, the size $L_f$(mm) of the defect can be accurately measured.

Through monomial regression analysis on the data attained in reference to FIGS. 8 and 9, the following regression expression 1 and expression 2 (designated by a solid line respectively in FIGS. 8 and 9) were attained.

$$\Delta V\ (dB) = 0.18 + 11.29 L_g\ (mm) \quad \text{[Expression 1]}$$

$$\min (V_2, V_3)(dB) = -82.64 + 9.57 L_f\ (mm) \quad \text{[Expression 2]}$$

In this case, since the correlation coefficients in the expressions are 0.99, a probability of that the data of the bonded body actually measured matches to the recurrence linear line indicated in the expression 1 or the expression 2 is quite high so long as the bonding condition and the measurement condition are the same.

Accordingly, if the relation between the difference Δ V and the size $L_g$ indicated in the expression 1 is calculated in advance using a sample bonded under the same condition as that of the actual bonded body, it is possible to estimate the size $L_g$ of the step fault produced at the edge of the bonding interface of the actual bonded body with high accuracy irrespective of presence of the defect by substituting the difference Δ V between the reflected echo heights actually measured into the attained relation.

Similarly, if the relation between the minimum values min ($V_1$, $V_2$) of the reflected echo heights and the size $L_f$ of the defect indicated in the expression 2 is calculated in advance, it is possible to estimate the size $L_f$ of the defect present at the edge of the bonding interface of the actual bonded body with high accuracy irrespective of presence of the step fault by substituting the minimum values min ($V_1$, $V_2$) of the reflected echo heights actually measured into the attained relation.

It should be noted here that this invention is not limited to the aforesaid preferred embodiment and various modifications may be made without departing from the principle of the present invention. For example, in the case of the aforesaid preferred embodiment, an ultrasonic wave is made enter toward the inner circumferential surface of the bonding interface of the metallic pipe. However, it is possible to shift the position of the probe, so that the ultrasonic wave is made enter toward the outer circumferential surface of the bonding interface after being reflected at the inner circumferential surface of the bonded body. As the result, the step fault and the defect present at the inner circumferential surface as well as at the outer circumferential surface are detected along with their sizes.

In addition, although the method for measuring the reflected echo height with the use of one, or one pair of, slant angled probes arranged on one metallic pipe has been described in the aforesaid preferred embodiment, it may also be possible to arrange more than two, or two pairs of, slant angled probes on one metallic pipe in parallel. The reflected echo heights are measured with the use of those slant angled probes. This allows to shorten a scanning distance in a direction in parallel with the bonding interface as well as the measurement time.

As has been described above, the method for evaluating bonding properties of a metallic pipe of the present invention is particularly suitable for examining a step fault and a defect produced at the edge of the bonded portion of a metallic pipe such as plant piping, a line pipe, an oil cell pipe or the like. Yet, the present invention can also be applied to a bonding portion where plate members are abutted against each other and bonded together to attain similar effects attained in the aforesaid preferred embodiments. Further, the present invention can also be applied to, in addition to the contact method as described above, a water immersion method.

Second Preferred Embodiment

Figure 10:
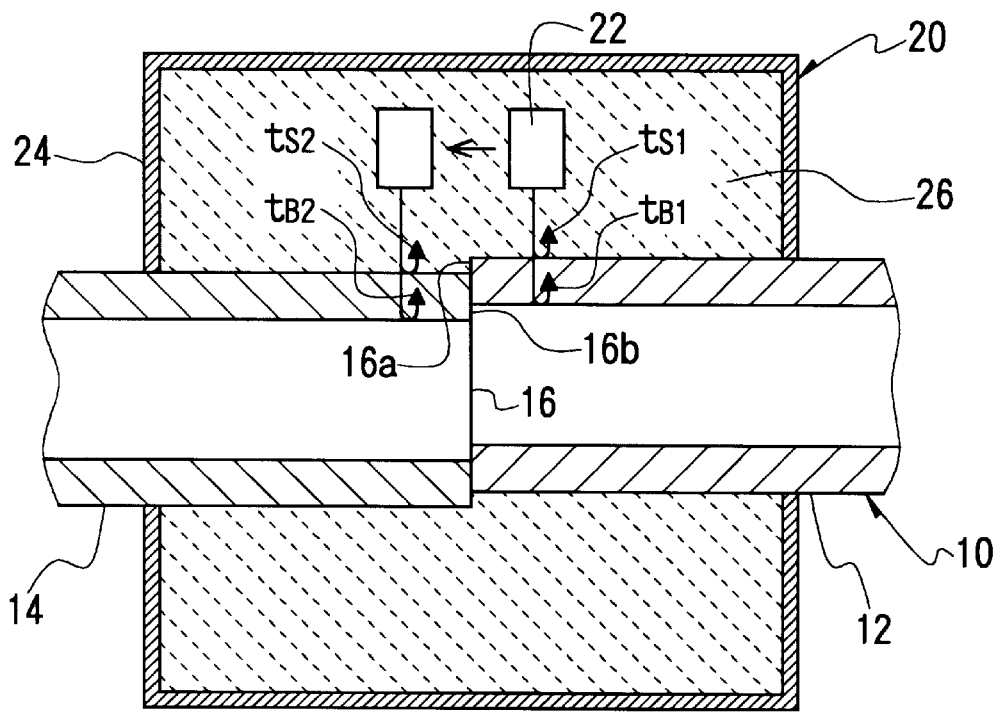
FIG. 10 is a schematic configuration view for showing one example of a method for evaluating bonding properties of a metallic pipe of the second preferred embodiment of the present invention.

FIG. 10 is a schematic configuration view for showing one example of an examining device used in a method for evaluating bonding properties and bonded body to be evaluated in a second preferred embodiment of the present invention.

In FIG. 10, the bonded body 10 is constructed by bonding the metallic pipe 12 and the metallic pipe 14 together at their ends by diffusion bonding. In the case of the bonded body 10 shown in FIG. 10, both an outer step fault 16a and an inner step fault 16b are present respectively on an outer circumferential surface and an inner circumferential surface of the bonding portion 16.

An inspecting device 20 is comprised of a ultrasonic wave probe 22 and a tank 24. The ultrasonic wave probe 22 is spaced a predetermined distance away from the outer circumferential surface of the bonded body 10 so as to enable the ultrasonic wave to enter vertically against the outer circumferential surface of the bonded body 10. In addition, the ultrasonic wave probe 22 can be moved in an axial direction and a circumferential direction by driving means, not shown. Further, in the case where the ultrasonic wave probe 22 is moved in an axial direction of the bonded body 10, it is desirable that a moving direction of the ultrasonic wave probe 22 and an axial direction of the bonded body 10 are in parallel to each other. Yet, a slight inclination may also be acceptable in the both directions.

In addition, a tank 24, as has already been described, is used for sealing an space surrounding the bonded portion 16 of the bonded body 10 for preventing a leakage of coupling medium 26 intervening between the ultrasonic wave probe 22 and the outer surface of the bonded body 10. The coupling medium 26 is used for attaining an efficient propagation of the ultrasonic wave, and to be more specific, water, oil, glycerin or the like are preferable. Here, in the case where the size of the bonded body 10 is relatively small, it may also be applicable to use a water tank or the like filled with coupling medium 26, instead of the tank 24, to place the entire bonding body 10 therein.

Next, there will be described a method for evaluating the bonding portion with the use of the inspecting device 20 shown in FIG. 10. First, the ultrasonic wave probe 22 is arranged outside one metallic pipe 12 adjacent to the metallic pipe 14 through the bonding portion 16. In this case, it is preferable that the ultrasonic wave probe 22 is arranged in the vicinity of the bonding portion 16.

Then, the ultrasonic wave is made enter vertically from the ultrasonic wave probe 22 against an outer circumferential surface of the metallic pipe 12 and then a reciprocating time $t_{S1}$ taken for the outer reflected echo reflected at the outer circumferential surface of the metallic pipe 12 to reach the ultrasonic wave probe 22 is measured. In addition, since the ultrasonic wave is incident to the metallic pipe 12 is partially transmitted into the metallic pipe 12 and is reflected also at the inner circumferential surface of the metallic pipe 12. Therefore, a reciprocating time $t_{B1}$ of the inner reflected echo may also be measured at this time concurrently.

Next, the ultrasonic wave probe 22 is moved along an axial direction of the bonded body 10 and arranged in the vicinity of the bonding portion 16 and outside the metallic pipe 14. Then, ultrasonic waver is made enter from the ultrasonic wave probe 22 perpendicularly against an outer circumferential surface of the metallic pipe 14, thereby measuring both a reciprocating time $t_{S2}$ of the outer reflected echo reflected at the outer circumferential surface of the metallic pipe 14 and a reciprocating time $t_{B2}$ of the inner reflected echo reflected at the inner circumferential surface of the metallic pipe 14.

In the case where only a size of the outer step fault 16a is calculated, it is satisfactory to measure only the reciprocating time $t_{S1}$, $t_{S2}$ of the outer reflected echo as described later. In other words, it is not necessary to measure the reciprocating time $t_{B1}$, $t_{B2}$ of the inner reflected echo.

Then, a size of the outer step fault 16a, a size of the inner step fault 16b and a thickness of the bonding portion 16 are calculated from the reciprocating time $t_{S1}$, $t_{S2}$ of the outer reflected echo as well as the reciprocating time $t_{B1}$, $t_{B2}$ of the inner reflected echo measured for each of the metallic pipes 12, 14.

Figure 12A:
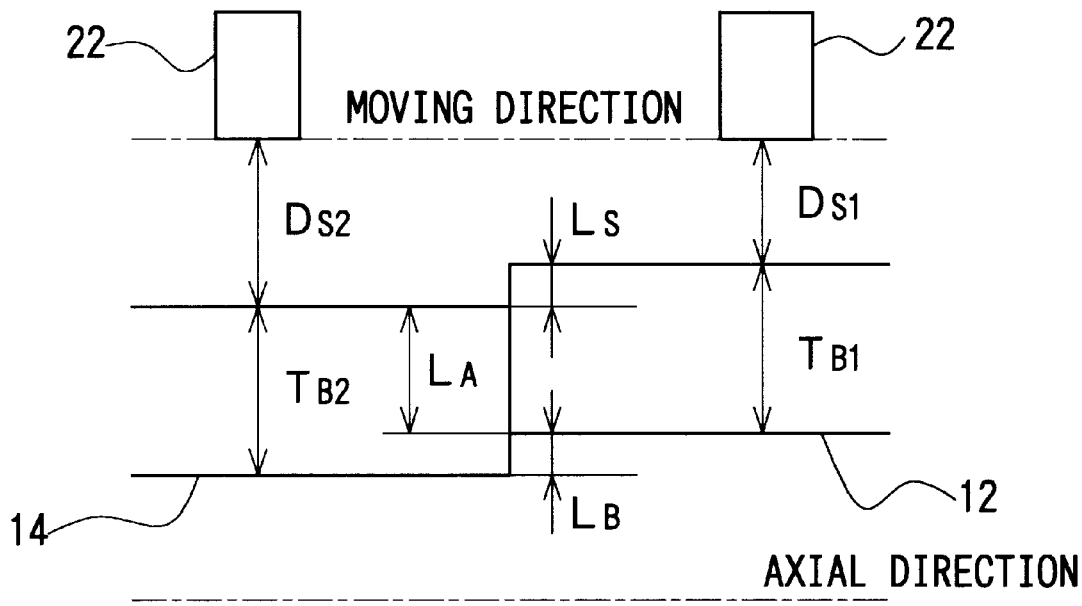
FIGS. 12A and 12B are views for illustrating a method for calculating an outer step fault and an inner step fault.

First, a method for calculating a size of the outer step fault 16a will be described. As shown in FIG. 12A, distances from the ultrasonic wave probe 22 to each of the metallic pipes 12 and 14 are defined as $D_{S1}$, $D_{S2}$, respectively. Provided that a moving direction of the ultrasonic wave probe 22 and an axial direction of the bonded body 10 are parallel to each other. In this case, a size $L_S$ of the outer step fault 16a is expressed by the following expression No. 3 as follows.

$$L_S = D_{S2} - D_{S1} \qquad \text{[Expression 3]}$$

Assuming that a sound velocity in the coupling medium 26 is defined as $C_W$, each of the reciprocating time $t_{S1}$, of the outer reflected echo of the metallic pipe 12 and the reciprocating time $t_{S2}$ of the outer reflected echo of the metallic pipe 14 is expressed by the following expression Nos. 4 and 5, respectively.

$$D_{S1}=C_W \times t_{S1}/2 \qquad \text{[Expression No. 4]}$$

$$D_{S2}=C_W \times t_{S2}/2 \qquad \text{[Expression No. 5]}$$

Substituting the expression Nos. 4 and 5 into the expression No. 3, the following expression No. 6 is attained.

$$L_S=C_W \times (t_{S2}-t_{S1})/2 \qquad \text{[Expression No. 6]}$$

Figure 12B:
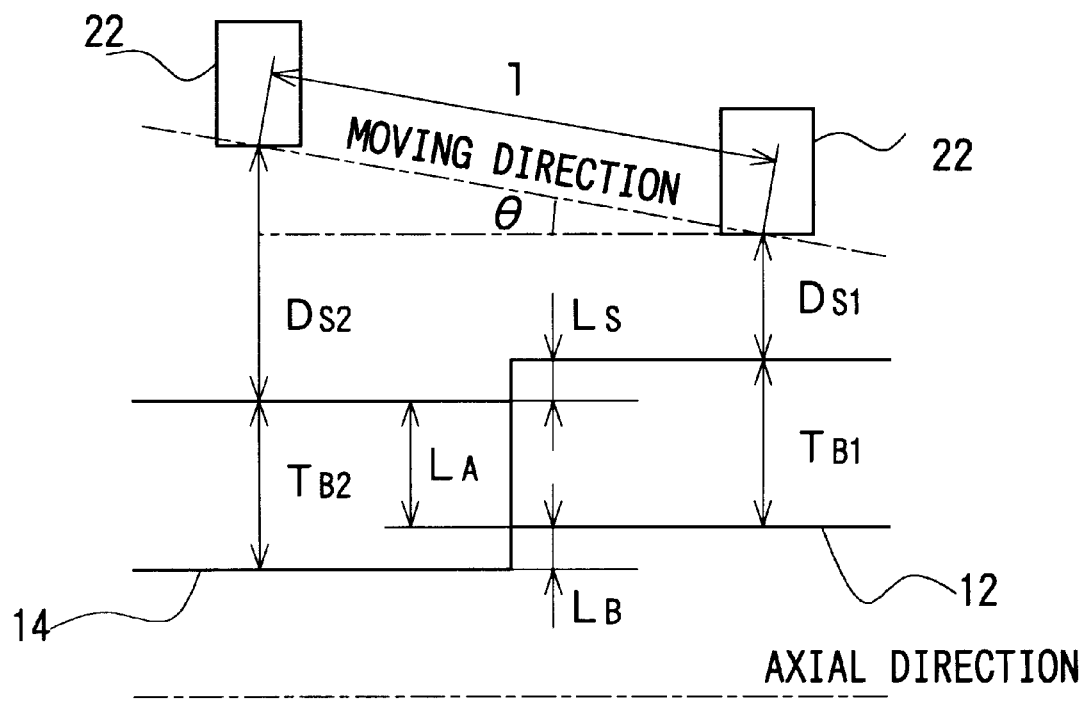

Accordingly, if the reciprocating time $t_{S1}$, and $t_{S2}$ of the outer reflected echo are measured, the size $L_S$ of the outer step fault 16a can be calculated. As shown in FIG. 12B, even in the case where there is a certain inclination between the moving direction of the ultrasonic wave probe 22 and the axial direction of the bonded body 10, the expression can be satisfactory corrected with a moving distance 1 of the ultrasonic wave probe 22 and a slant angle θ, which are measured separately to correct the expression No. 6.

There are various kinds of methods for measuring the moving distance 1 and the slant angle θ, with no particular restriction. For example, to attain the moving distance 1, a displacement sensor is provided to driving means for the ultrasonic wave probe 22. The moving distance 1 is easily obtained from values that the displacement sensor indicates. In addition, the slant angle θ can be attained by performing a continuous measurement of the reciprocating time of the outer reflected echo as the ultrasonic wave probe 22 is moved in an axial direction of the bonded body 10. The slant angle θ is obtained from the amount of variation in time.

Next, a method for calculating a size of the inner step fault 16b will be described. As shown in FIG. 12A, there will be considered the case where the wall thicknesses of the metallic pipe 12 and the metallic pipe 14 are respectively defined as $T_{B1}$, $T_{B2}$ and the ultrasonic wave probe 22 is moved in parallel to an axial direction of the bonded body 10. In this case, a size $L_B$ of the inner step fault 16b is expressed by the following expression No. 7.

$$L_B=(D_{S2}+T_{B2})-(D_{S1}+T_{B1}) \qquad \text{[Expression No. 7]}$$

Assuming that a sound velocity with which the ultrasonic wave travels through the metallic pipes 12, 14 is defined as $C_M$, $T_{B1}$ and $T_{B2}$ are respectively expressed by the following expression Nos. 8 and 9 with the use of reciprocating time $t_{S1}$ and $t_{B1}$ of the outer and inner reflected echoes of the metallic pipe 12 as well as the reciprocating time $t_{S2}$ and $t_{B2}$ of the outer and inner reflected echoes of the metallic pipe 14.

$$T_{B1}=C_M \times (t_{B1}-t_{S1})/2 \qquad \text{[Expression No. 8]}$$

$$T_{B2}=C_M \times (t_{B2}-t_{S2})/2 \qquad \text{[Expression No. 9]}$$

Substituting Expression Nos. 4, 5, 8 and 9 into the Expression No. 7, the following expression No. 8 is attained.

$$L_B=(C_W-C_M) \times (t_{S2}-t_{S1})/2+C_M \times (t_{B2}-t_{B1})/2 \qquad \text{[Expression No. 10]}$$

Accordingly, it is apparent that if the reciprocating time $t_{S1}$ and $t_{S2}$ of the outer reflected echoes as well as the reciprocating time of $t_{B1}$ and $t_{B2}$ of the inner reflected echoes are measured, the size $L_B$ of the inner step fault 16b can be calculated. In addition, even in the case where there is an inclination between the moving direction of the ultrasonic wave probe 22 and the axial direction of the bonded body 10, similarly to the case of the Expression No. 6, the Expression No. 10 can be satisfactory corrected with the moving distance 1 of the ultrasonic wave probe 22 and an inclination angle θ, which are separately measured.

Then, there will be described a method for calculating a thickness of the bonding portion 16. The thickness of the bonding portion $L_A$ can be easily calculated with the use of $D_{S1}$ calculated from the expression No. 4, $D_{S2}$ calculated from the expression No. 8, $T_{B1}$ calculated under the expression No. 9, and $T_{B2}$ calculated from the expression No. 9. That is, in the case where the ultrasonic wave probe 22 is moved in parallel to an axial direction of the bonded body 10, the bonded thickness $L_A$ is expressed by the following expression 11 under an assumption that, as apparent from FIG. 12A, a larger value between $D_{S1}$ and $D_{S2}$ is defined as $D_1$ and a smaller value between $(D_{S1}+T_{B1})$ and $(D_{S2}+T_{B2})$ is defined as $D_2$.

$$L_A=D_2-D_1 \qquad \text{[Expression 11]}$$

Accordingly, it is apparent that once the reciprocating time $t_{S1}$ and $t_{S2}$ of the outer reflected echoes and the reciprocating time $t_{B1}$ and $t_{B2}$ of the outer reflected echoes are measured, the thickness $L_A$ of the bonding portion can be calculated. In addition, since $L_A$ indicates a thickness of the bonding portion 16 at a certain point, if the ultrasonic wave probe 22 is moved in sequence in a circumferential direction to calculate $D_{S1}$, $D_{S2}$, $T_{B1}$ and $T_{B2}$, a total area of the bonding portion 16 is as well calculated. In addition, even in the case where there is an inclination between the moving direction of the ultrasonic wave probe 22 and the axial direction of the bonded body 10, similarly to the case of the expression Nos. 6 and 10, the expression No. 11 can be corrected with the moving distance 1 and the inclination angle θ, which are measured separately.

As described above, in accordance with the method for evaluating the bonding portion of the second preferred embodiment, through measuring the reciprocating time of the outer reflected echoes and the reciprocating time of the inner reflected echoes at both sides bonded together through the bonding portion 16, the size $L_S$ of the outer step fault 16a, the size $L_B$ of the inner step fault 16b and the bonded thickness $L_A$ are easily calculated.

Different from conventional methods using the use of slide calipers to measure a size of the step fault, it is not necessary that the measuring instrument be in a direct contacted with the bonded body 10, and therefore, under the size accuracy or a degree of flatness is poor as often found in the seamless steel pipe, it is still possible to accurately and efficiently measure of a size of the step fault or the like.

Third Preferred Embodiment

Hereinafter, there will be described a method for evaluating a bonding portion in accordance with the third preferred embodiment of the present invention. The method for evaluating the bonding portion in accordance with the third preferred embodiment is similar to that of the second preferred embodiment in that the operation that both reciprocating time $t_{S1}$, $t_{S2}$ of the outer reflected echo as well as the reciprocating time $t_{B1}$, $t_{B2}$ of the inner reflected echo are measured to calculate the size $L_S$ of the outer step fault 16a, the size $L_B$ of the inner step fault 16b and the bonded thickness $L_A$. Yet, the method in this embodiment is different from that of the second embodiment in view of the fact that the reciprocating time $t_{S1}$, $t_{S2}$ of the outer reflected echo and reciprocating time $t_{B1}$, $t_{B2}$ of the inner reflected echo are not measured concurrently, but are measured at different locations.

Figure 11:
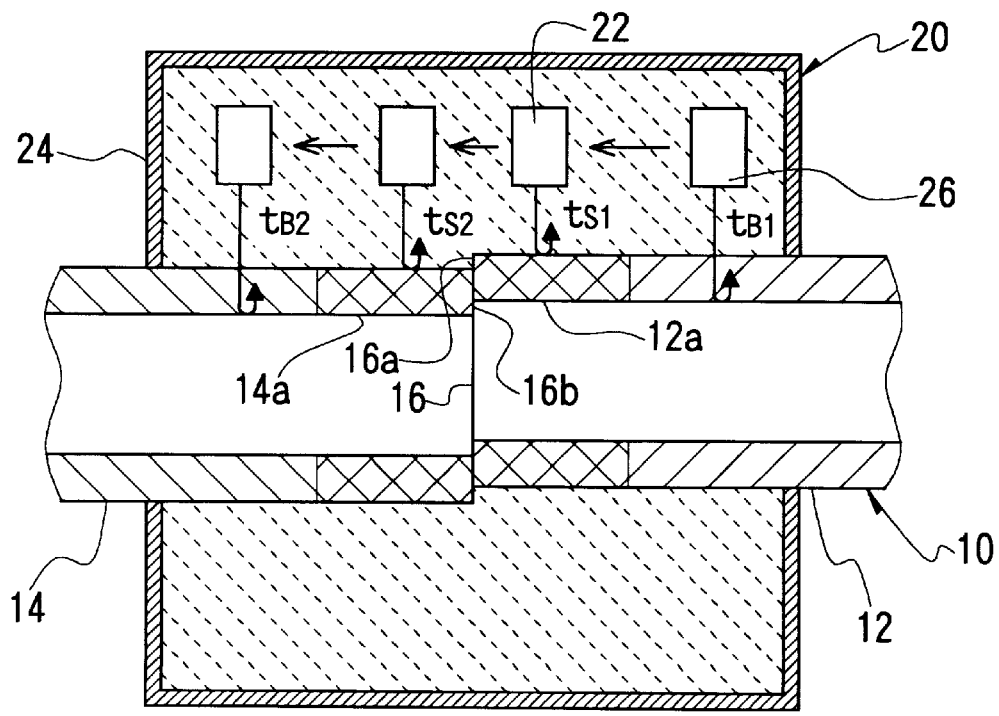
FIG. 11 is a schematic configuration view for showing one example of a method for evaluating bonding properties of a metallic pipe of the third preferred embodiment of the present invention.

That is, in this preferred embodiment of the present invention, first the ultrasonic wave probe 22 is arranged outside a heat-affected part 12a of the metallic pipe 12, which has been affected by thermal history at the time of bonding, as shown in FIG. 11, and then reciprocating time $t_{B1}$ of the inner reflected echo is measured. Next, the ultrasonic wave probe 22 is moved in an axial direction of the metallic pipe 12, arranged near the bonding portion 16 and arranged outside the metallic pipe 12 and then a reciprocating time $t_{S1}$ of the outer reflected echo is measured.

Then, the ultrasonic wave probe 22 is moved in an axial direction of the metallic pipes 12,14, arranged near the bonding portion 16 and outside the metallic pipe 14 and a reciprocating time $t_{S2}$ of the outer reflecting echo is measured. In addition, the ultrasonic wave probe 22 is moved in an axial direction of the metallic pipe 14, arranged outside the thermal influencing part 14a of the metallic pipe 14 and then the reciprocating time $t_{B2}$ of the inner reflected echo is measured.

In addition, an operation that a size $L_S$ of the outer step fault 16a, a size $L_B$ of the inner step fault 16b and the bonded thickness $L_A$ are sufficiently calculated in reference to the aforesaid expression Nos. 3 to 11, and an operation that the moving distance 1 and the inclination angle θ are separately measured in the case where the moving direction of the ultrasonic wave probe 22 and the axial direction of the bonded body 10 are inclined from each other and $L_S$, $L_B$ and $L_A$ are amended with the use of these values are similar to that of the second preferred embodiment.

In accordance with the method for evaluating the bonding portion of the third preferred embodiment, since the reciprocating time $t_{S1}$, $t_{S2}$ of the outer reflected echo are measured near the bonding portion 16, the size $L_S$ of the outer step fault 16a can be measured accurately even if the part near the bonding portion 16 is deformed under heated condition of the bonding portion 16 during its connection.

In addition, since the heat-affected parts 12a, 14a have rough increased grain particles under heated condition at the time of connecting operation, there occurs a possibility that dispersion of ultrasonic wave is increased or an elastic modules is changed. Due to this fact, if the reciprocating time $t_{B1}$, $t_{B2}$ of the inner reflected echo in the heat-affected parts 12a, 14a are measured, the inner reflected echo may not be attained or an error in measurement may possibly be increased. To the contrary, as shown in the third preferred embodiment of the present invention, if the reciprocating time $t_{B1}$, $t_{B2}$ of the inner reflected echo are measured outside the heat-affected parts 12a and 14a, influence caused by heating operation can be avoided and the inner reflected echo can be detected with high sensitivity and high accuracy.

Even if a measuring position for the reciprocating time $t_{S1}$, $t_{S2}$ of the outer reflected echo is spaced apart from a measuring position for the reciprocating time $t_{B1}$, $t_{B2}$ of the inner reflected echo, an error produced at each of the wall thicknesses $T_{B1}$, $T_{B2}$ in the expression Nos. 8 and 9 is low and so it is possible to measure step fault sizes $L_S$, $L_B$ and the bonded thickness $L_A$ in a high accuracy.

This is due to the tendency that the wall thickness is substantially kept constant across the bonding portion in general in view of the fact that when the place near the bonding portion is deformed by the diffusion bonding operation, the pipe wall is only deformed in an outward or an inward direction. In addition, even in the case where the seamless steel pipes having poor size accuracy are used as the metallic pipes 12, 14, the wall thickness of each of the seamless steel pipes has large disturbance in a circumferential direction in general and low disturbance in an axial direction.

Second Example

As to the bonded body 10 in which the seamless steel pipes are bonded in liquid phase diffusion, an outer step fault $L_S$, an inner step fault $L_B$ and a bonded thickness $L_A$ were measured by using the inspection device 20 shown in FIG. 10. In addition, as the coupling medium 26, water was used and the measurement was carried out over an entire circumference of the bonding portion 16 of the bonded body 10. Results of measurement are indicated in FIGS. 13A, B and C, respectively.

Figure 13A:
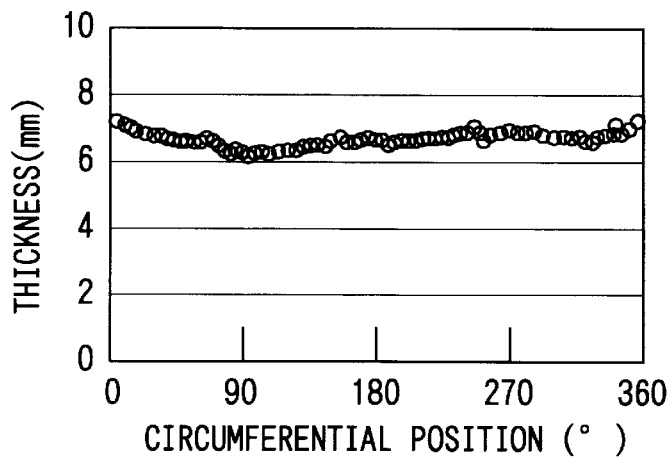
FIG. 13A is a view for showing a variation in a wall thickness of the metallic pipe in a circumferential direction measured with the use of the evaluating method of the present invention.

In FIG. 13A is indicated a wall thickness $t_{B1}$ of one metallic pipe 12 calculated with the use of the expression No. 8. From FIG. 13A, it becomes apparent that the wall thickness $T_{B1}$ of the seamless steel pipe used in the preferred embodiment is varied in a range of about 6 to 7 mm.

Figure 13B:
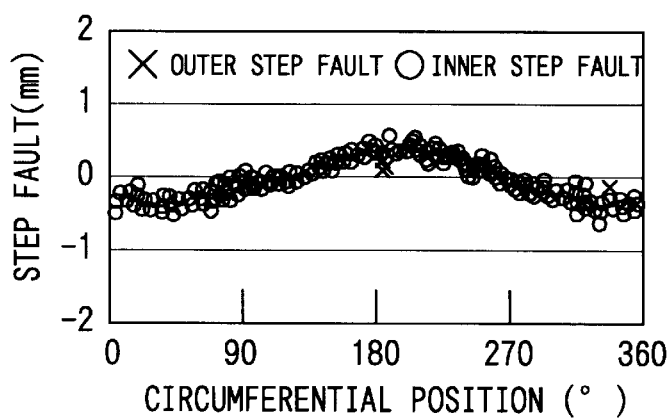
FIG. 13B is a view for showing a variation of an outer step fault and an inner step fault in a circumferential direction.

In addition, in FIG. 13B are indicated a size $L_S$ of the outer step fault 16a calculated with the use of the expression No. 6 and a size $L_B$ of the inner step fault 16b calculated with the use of the expression No. 10. From FIG. 13B, it becomes apparent that a size $L_S$ of the outer step fault 16a is about 0.2 mm at any positions and in turn a size $L_B$ of the inner step fault 16b is varied in a range of ±0.5 mm in response to a circumferential position. This is due to the fact that an axial alignment is performed between the metallic pipes 12, 14 in such a way that the outer step fault 16a becomes minimum when the pipes are bonded.

Figure 13C:
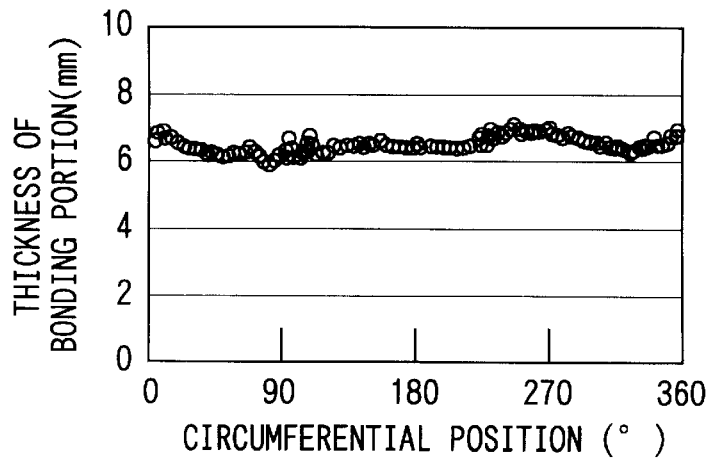
FIG. 13C is a view for showing a variation of a thickness of a bonding portion in a circumferential direction.

Further, in FIG. 13C is indicated a bonded thickness $L_A$ calculated with the use of the expression No. 11. From FIG. 13C, it becomes apparent that the bonded thickness $L_A$ is varied within a range of 6 to 7 mm in response to a circumferential position. These results coincided well with a wall thickness $T_{B1}$ of each of the portions, a size $L_S$ of the outer step fault 16a, a size $L_B$ of the inner step fault 16b and a bonded thickness $L_A$ actually measured after cutting the attained bonded body.

Although the second and third preferred embodiments of the present invention have been described in detail as above, the present invention is not limited to the aforesaid preferred embodiments and various modifications of the present invention can be carried out within a range not departing from the gist of the present invention.

For example, although the aforesaid second preferred embodiment is constructed such that one ultrasonic wave probe 22 is moved in an axial direction of the bonded body 10, the reciprocating time of the outer reflected echo and the reciprocating time of the inner reflected echo of the adjoining two metallic pipes 12 and 14 through the bonding portion 16 are measured, it may also be applicable that the two ultrasonic wave probes 22 are arranged in an axial direction of the bonded body 10 with the bonding portion 16 being held therebetween, a ultrasonic wave is incident in a vertical direction and from the same direction against each of the metallic pipes 12, 14 without moving the ultrasonic wave probe 22, thereby the reciprocating time of the reflected echo may be measured.

Similarly, in the third preferred embodiment, in place of performing an axial motion of one ultrasonic wave probe 22 against the bonded body 10, it may also be applicable that each of the two ultrasonic wave probes 22 is arranged in an axial direction of the bonded body 10 outside the adjoining two metallic pipes 12, 14 and the reciprocating time of the reflected echo are measured without moving these ultrasonic wave probes 22.

In addition, in the second and third preferred embodiments above, although the ultrasonic wave probes 22 are moved, it may also be applicable that the ultrasonic wave probes 22 are fixed, the bonded body 10 is moved in respect to the ultrasonic wave probes 22, thereby a ultrasonic wave is incident in a vertical direction and from the same direction against each of the metallic pipes 12, 14, thereby the reciprocating time of the outer reflected echo and the reciprocating time of the inner reflected echo may be measured.

In addition, it is also applicable that two or more ultrasonic wave probes 22 are arranged in an axial direction and a circumferential direction of the bonded body 10 and the reciprocating time are measured with the use of these elements. If both the reciprocating time of the outer reflected echo and the reciprocating time of the inner reflected echo are measured concurrently with the use of a plurality of ultrasonic wave probes 22 as described above, it is advantageous in that a size of the step fault and a connecting thickness or the like and their circumferential variation can be measured concurrently without moving the ultrasonic wave probes 22. In addition, the ultrasonic wave probes 22 are moved in a circumferential direction to enable a circumferential variation of a size of the step fault and the connecting thickness to be measured.

Fourth Preferred Embodiment

Figure 14:
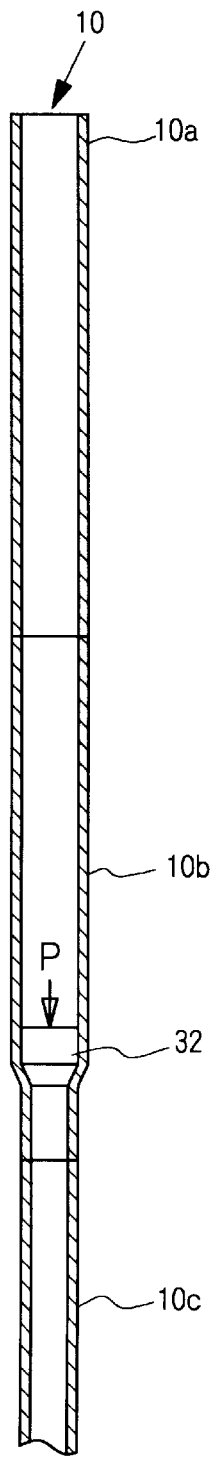
FIG. 14 is a view for showing a technical concept to illustrate a pipe expansion step of a metallic bonded pipe of one preferred embodiment of the present invention.

Next, in FIG. 14 is shown by a schematic concept view a state in which the metallic bonded pipes having metallic pipes bonded from each other is expanded in its diameter as a fourth preferred embodiment of the present invention. Pipe members 10a, 10b and 10c are bonded in sequence by diffusion-connection to make a metallic bonded pipe 10. Then, a pipe expanding mandrel 32 is inserted from one opening end of the metallic bonded pipe 10, a predetermined load P is applied to it, the pipe expanding mandrel 32 is pushed into the metallic pipe, with the result that the inner wall surface of each of the pipe members 10a, 10b and 10c is pushed outwardly as shown in the figure, and its diameter is expanded.

Figure 15:
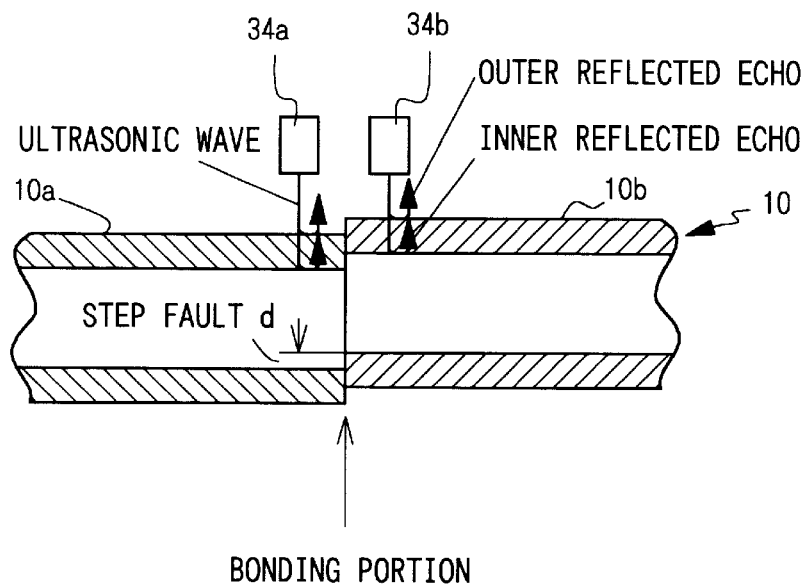
FIG. 15 is an illustrative view for showing a method for measuring a step at the bonding portion of a metallic pipe by an ultrasonic measurement.

Next, there will described a method for measuring a step fault at the inner circumferential surface of the metallic bonded pipe 10 at the bonding portion 16. FIG. 15 shows a state for the method, wherein when the step fault (d) at the inner circumferential surface of the metallic bonded pipe 10 at the bonding portion is measured, a reflection method is applied, ultrasonic wave probes 34a and 34b are applied to the outer surface near each of the pipe members 10a, 10b, each of the ultrasonic waves produced from the ultrasonic wave probes 34a, 34b is incident in perpendicular to the outer surfaces of the pipe members 10a, 10b.

At this time, since the ultrasonic wave is reflected at the outer surface and the inner surface of the metallic pipe and detected by the ultrasonic wave probes 34a, 34b, both the reflected echo at the outer surface of the metallic pipe and the reflected echo from the inner surface of the metallic pipe are detected and a step fault (d) of the inner circumferential surfaces of both pipe members 10a, 10b at the bonding portion is calculated by an arithmetic operation in reference to a time gap between the reciprocating reflected echoes.

More practically, it is assumed that a reciprocating time of reflected echoes at the outer circumferential surface measured by the ultrasonic wave probe 34a for one pipe member 10a is defined as $t_{S1}$, a reciprocating time of a reflected echo at the inner circumferential surface is defined as $t_{B1}$, a reciprocating time of a reflected echo at the outer circumferential surface measured by the ultrasonic wave probe 34b of the other pipe member 10b is defined as $t_{S2}$ and a reciprocating time of the reflected echo at the inner circumferential surface is defined by $t_{B2}$. Then, a size of step fault $L_B$ of the inner circumferential surface of both pipe members 10a, 10b at the bonding portion is expressed by the above-mentioned expression No. 10 and then the size of step fault $L_B$ of the inner circumferential surface is calculated by this arithmetic expression.

Figure 16:
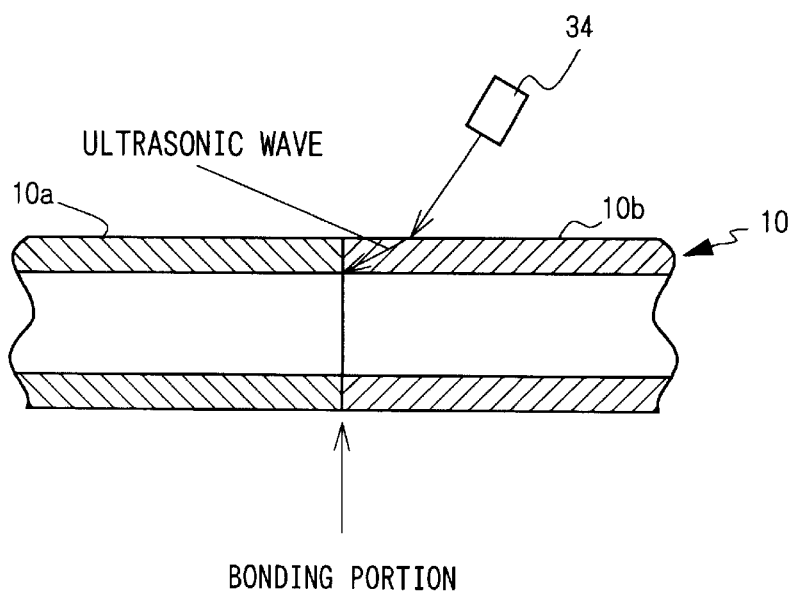
FIG. 16 is an illustrative view for showing a method for measuring a presence of a defect at the bonding portion of a metallic pipe by an ultrasonic wave (reflected echo) measurement.

In addition, FIG. 16 indicates a method for measuring presence of defect at the bonding portion of the metallic pipes. In this case, a reflecting method is also applied, a ultrasonic wave probe 34 is applied to the outer surface near one pipe member 10a (or 10b), the ultrasonic wave produced from the ultrasonic wave probe 34 is incident in slant toward the bonding interface of the metallic bonded pipe 10.

In the case where there is present a defect at the bonding interface, the ultrasonic wave is reflected at the defect, so that the reflected wave is detected by the ultrasonic wave probe 34, presence of the defect or its size at the bonding portion of the metallic bonded pipe 10 is calculated in reference to the size of the detected reflected wave. If there is a crack or a void at the bonding portion, the reflected echo becomes large, so that such a pipe is eliminated. Here, a step fault and a defect such as a crack may be distinguished from each other by the method in the above-described first invention.

Figure 17:
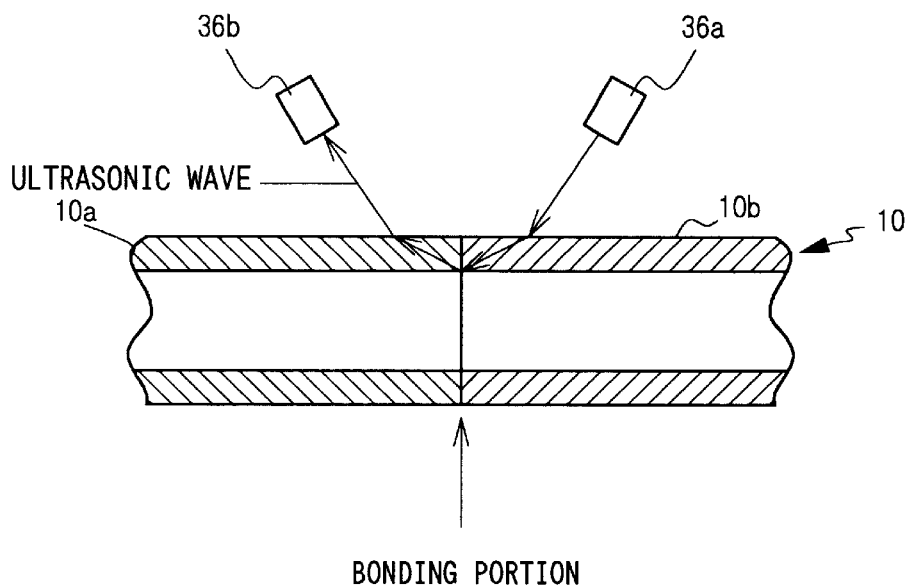
FIG. 17 is an illustrative view for showing a method for measuring a variation of metallic structure at the bonded portion of the metallic pipe by an ultrasonic (transmission echo) measurement.

In addition, FIG. 17 indicates a method for measuring a degree of variation of the crystal structure of the metallic bonded pipe 10 at the bonding portion. In this case, a transmission method is applied, a ultrasonic wave probe 36a is applied to the outer surface of one pipe member 10b near the bonding portion of the metallic bonded pipe 10 and a ultrasonic wave probe 36b is applied to the outer surface of the other pipe member 10a.

Then, the ultrasonic wave produced from the ultrasonic wave transmission probe 36a is incident in a slant manner toward the bonding interface of the metallic bonded pipe 10, the ultrasonic wave passed through the bonding interface is detected by the ultrasonic wave receiving probe 36b and a degree of variation of the crystal structure at the bonded location of the metallic bonded pipe 10 is calculated in reference to a size of the detected ultrasonic wave echo. If the grain particles or the crystal structure is fine, the ultrasonic wave echo is high, although if the crystal structure is changed into rough large size, the ultrasonic wave echo is reduced, resulting in elimination of such a pipe as above.

Although the aforesaid preferred embodiment relates to a method for searching a flaw with ultrasonic wave such by a water immersion process, this invention is not limited to this form, but it may also be applicable that a direct contact method for directly contacting the ultrasonic wave probe to a test material through coupling medium is performed.

Third Example

Then, the ultrasonic examination for the metallic bonded pipe with the use of the test material was actually carried out. Its result will be described as follows. As the test material, it was a steel pipe having as material quality a low carbon steel STOG410 (JIS G 3454) and the pipe with an outer diameter of 5.5"×wall thickness of 6.5 mm×length 330 mm was used. Its chemical components are indicated in Table 2 as follows. The metallic bonded pipes of the test material are bonded by a liquid phase interface connecting process and as the insert material, Ni-system alloy is used. As a practical connecting condition, the connecting temperature was in a range of 1250° C. to 1400° C., a compressing force was in a range of 1.5 MPa to 5 MPa and heating connection was carried out for 100 to 200 seconds and 32 pipes (test material Nos. "1" to "32") were prepared.

TABLE 2

| | STPG410 (JIS G 9464) | | | | |
|---|---|---|---|---|---|
| | C | Si | Mn | P | S |
| CHEMICAL COMPOSITION | 0.30 or less | 0.35 or less | 0.30 ~ 1.00 | 0.040 or less | 0.040 or less |

Figure 18:
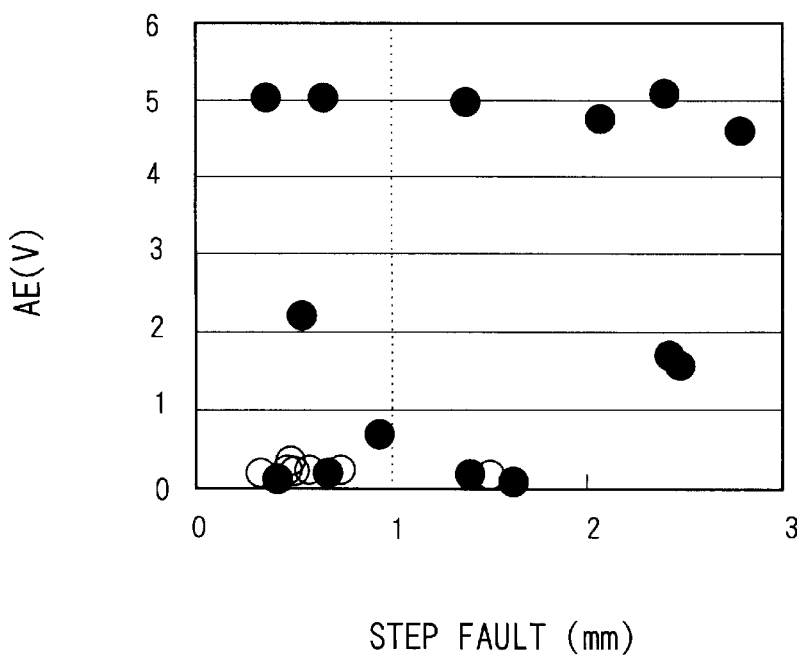
FIG. 18 shows an example of measurement showing a relation between a step fault at a bonded portion and a result of pipe expansion.
Figure 19:
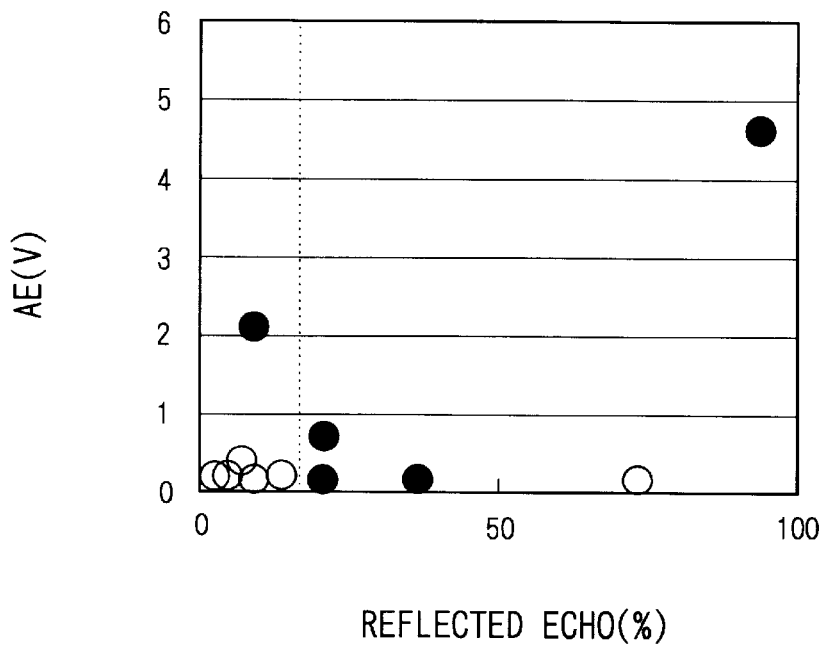
FIG. 19 shows an example of measurement showing a relation between a reflection echo height at a bonded portion and a result of pipe expansion.
Figure 20:
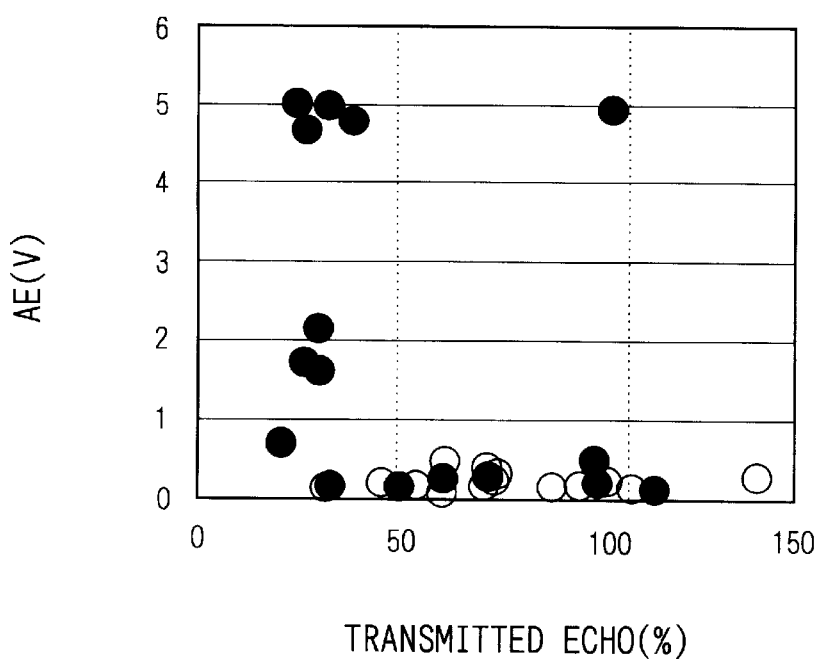
FIG. 20 shows an example of measurement showing a relation between a echo height of an ultrasonic wave which transmits the bonded portion and a result of pipe expansion.

As to these test materials, the pipes were expanded at their diameter by the pipe expanding mandrel under a condition of pipe expansion rate of 20% and a pipe expansion velocity of 70 mm/min and quality evaluation at the bonded surfaces was carried out through an ultrasonic examination process. The results are shown in FIGS. 18 to 20 and will be described as follows. The device with which the above pipe expansion process was monitored was an acoustic emission detecting probe.

FIG. 18 shows a state in which a degree of discontinuity in shape, more practically, a relation between the step fault at the bonding portion and the result of expanding pipes was measured in reference to each of the test materials (Nos. 1 to 32). A step fault (mm) is set at X-axis and an intensity (V) of an AE signal is set at Y-axis, respectively. A degree of discontinuity (a step fault at the bonding portion) in shape is measured with the use of a vertical ultrasonic wave with a frequency of 30 MHz.

As apparent from data shown in FIG. 18, it is finally judged that almost of all test materials are defective products if the step fault at the bonding portion exceeds 1 mm, with the result that the material exceeding the step fault size of 1 mm in reference to this data is judged as a defective material and a threshold value A of the step fault (mm) is set to "1 mm".

In addition, FIG. 19 indicates an example of measurement of a relation between the reflected echo height at the bonding portion and the result of expanding pipe for each of the test materials (Nos. 1 to 32). A reflected echo (%) is set at X-axis and an intensity (V) of an AE signal is set at Y-axis. The data shown in FIG. 19 shows a possibility that as the reflected echo at the bonding portion exceeds 15%, the test material is finally judged as a defective one, with the result that the material with the reflected echo at the bonding portion exceeding 15% is judged as a defective product in reference to this data and a threshold value B of the reflected echo (%) is set to "15%".

Further, FIG. 20 indicates an example of measurement about a transmission echo height and the pipe expansion at the bonding interface for each of the test materials (No. 1 to No. 32). A transmitted echo (%) is plotted against an X-axis and an intensity (V) of an AE signal is plotted against a Y-axis. In case of the data shown in FIG. 20, the grain particles are changed into rough large-sized particles due to an excessive high heating temperature if the transmitted echo at the bonding interface is less than 50%, and in turn in the case where the transmission echo exceeds 100%, the grain particles are kept small due to an excessive low heating temperature, resulting in that a lower limit threshold value C of the transmission echo (%) is set to "50%" and an upper threshold value D is set to "100%".

Figure 21:
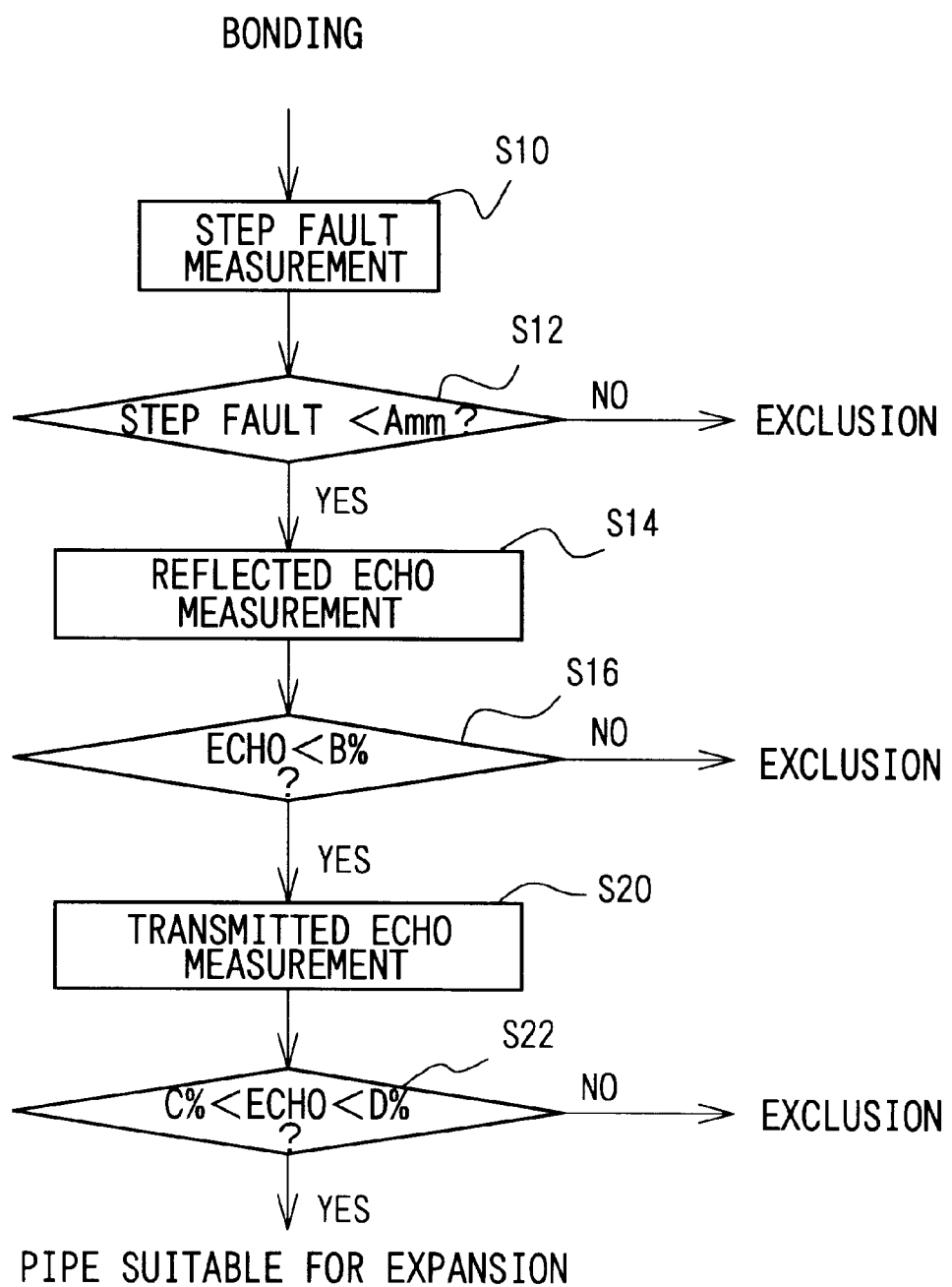
FIG. 21 is a flow chart illustrating a procedure of a evaluation of the bonding properties of the bonded portion of the metallic pipe with the use of an ultrasonic measurement of the present invention.

In this invention, the pipe which may cause a crack or the like to be produced finally when the pipe is expanded is eliminated in advance under a measurement performed under these ultrasonic examination processes in reference to the data shown in FIGS. 18 to 20. In FIG. 21 is indicated a flow chart illustrating a flow of step for evaluating quality at the bonding portion of the metallic bonded pipe of this invention. In this flow chart, a step fault measurement is performed at first (S10) before expanding the metallic bonded pipe 10, and in the case where it is judged that the step fault exceeds the threshold value A mm in FIG. 18 under this step fault measurement (S12 "No"), the pipe is removed due to the fact that its quality is judged a defective even if the pipe is expanded, and only the pipe which is discriminated that the step fault is less than the threshold value A mm (S12 "YES") is applied for measurement of the subsequent reflected echo (S14).

Then, in the case where it is judged that a measured value of the reflected echo exceeds a threshold value B in FIG. 19 (S16 "No"), it is of course apparent that quality of the pipe becomes defective, the pipe is removed and only the pipe in which a measured value of the reflected echo is judged to be less than a threshold value B% (S16 "YES") is set to be measured for measurement of the transmission echo (S18).

Then, it is apparent that the pipe in which a measured value of a transmission echo is judged to be less than a threshold value C% shown in FIG. 20 or more than a threshold value D% (S22 "No") shows a defective quality, so that the pipe judged to have a measured value of transmitted echo within a range of threshold values C% to D% (S22 "YES") is finally judged as an expandable pipe.

FIGS. 22A to D show the results in which each of the test materials (Nos. 1 to 32) was measured with ultrasonic wave in reference to an evaluation process. In each of the figures, a mark ● indicates a test material cracked at the bonding portion during expanding operation and a mark ○ indicates a test material not cracked at the bonding portion during expanding operation.

As a result, at first in the case where an evaluation test for a pipe expansion characteristic is not performed, it is natural that there are many test materials having inferior quality (FIG. 22A), and at the step where an evaluation test is performed with the use of ultrasonic wave measurement as a first step for it, a certain number of test materials are excluded as shown in FIG. 22B.

Then, the materials of a defective quality are excluded with the use of an evaluation of reflected echo test (FIG. 22C) and only the test materials judged as "expandable one" with the use of evaluation of transmitted echo are left (FIG. 22D). In the case where an evaluation test about an expanding characteristic of material was not performed, the number of test materials with a mark ○ was 16, and after performing this evaluation test measurement, this number was reduced to 13 and so this result showed that materials having a relative high safety characteristic were attained.

Accordingly, application of this ultrasonic wave measurement composed of these three steps avoids some disadvantages that a crack is produced at the bonding portion during pipe expanding process, or the metallic pipes are separated at the bonding portion and the pipes cannot be used as a pipe line or an oil well pipe and the like. Then, although it is not restricted in particular in what order the ultrasonic wave measurement composed of these three steps is carried out, it is effective that at first, a measurement at the step fault is performed, thereby a metallic bonded pipe producing an inferior expansion in diameter is excluded at an early step, presence of defect at the bonding portion is measured with the use of measurement of the reflected echo or a degree of variation of crystal structure at the bonding interface is measured with the use of measurement of the transmitted echo.

This invention is not limited to the aforesaid fourth preferred embodiment and various modifications can be attained without departing from a gist of this invention. In the aforesaid preferred embodiment, a low carbon steel pipe is indicated as material quality of metallic bonded pipe, for example. This is not restricted and this embodiment is applied to various kinds of material such as various kinds of carbon steels, stainless steels such as a martensite stainless steel, a binary stainless steel, an austenite stainless steel or the like.

In the aforesaid preferred embodiment, all the measurement at the inner surface step fault of the metallic bonded pipes, measurement of presence of a defect at the bonding portion and measurement of variation of crystal structure at the bonding interface are carried out, although as to the measurement of the inner surface step fault, it is not carried out by the ultrasonic examination process, but it may also be applicable to employ a process that, as disclosed in the Japanese Patent Application No. Hei 11 (1999)-181638 (not yet published), each of an outer diameter size and a wall thickness of the metallic pipes to be bonded to each other is measured in advance and an outer diameter step fault size after their connection is measured, thereby an inner diameter step fault size is calculated.

Although the liquid phase diffusion bonding method is the most preferable one as a method for connecting metallic pipes from each other, it is of course apparent that the solid phase diffusion bonding method can be applied. In the case of performing the liquid phase diffusion bonding method, Ni-based alloy or Fe-based alloy and the like are applied as an insert material for the bonding interface.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A method for evaluating bonding properties of a metallic pipe comprising:
   a first measurement step of measuring an echo height of an ultrasonic wave reflected back from an edge of a bonding interface where two pipe members are bonded together by diffusion bonding upon letting in an ultrasonic wave toward a first side of the bonding interface;
   a second measurement step of measuring an echo height of an ultrasonic wave reflected back from said bonding interface upon letting in the ultrasonic wave toward a second side of said bonding interface;
   a step fault determination step of determining whether or not there is a step fault present at said bonding interface based on a difference between the echo height measured in the first measurement step and the echo height measured in the second measurement step; and
   a defect determination step of determining whether or not there is a defect present at said bonding interface based on minimum values of the echo height measured in the first measurement step and the echo height measured in the second measured step.

2. The method for evaluating bonding properties of a metallic pipe according to claim 1, wherein the echo height measured in the first measurement step and the echo height measured in the second measurement step are compared to determine that there is a step fault if one of the echo heights is within a noise echo level while the other echo height exceeds the noise echo level.

3. The method for evaluating bonding properties of a metallic pipe according to claim 1, wherein the echo height measured in the first measurement step and the echo height measured in the second measurement step are compared to determine that there is a defect present if both of the noise echo heights exceed a noise echo level to the same extent.

4. The method for evaluating bonding properties of a metallic pipe according to claim 1, wherein the echo height measured in the first measurement step and the echo height measured in the second measurement step are compared to determine that there are both a step fault and a defect present if both of the echo heights exceed a noise echo level but to a different extent.

5. A method for evaluating bonding properties of a metallic pipe comprising:
   arranging an ultrasonic probe around an outer circumferential surface of a first pipe member of the metallic pipe being bonded together by diffusion bonding, and measuring reciprocating time, by said ultrasonic probe, for an ultrasonic wave incident perpendicularly toward the outer circumferential surface of said pipe member to reflect back its echo therefrom;
   arranging an ultrasonic probe around an outer circumferential surface of a second pipe member of the metallic pipe, and measuring reciprocating time, by the ultrasonic probe, for an ultrasonic wave incident perpendicularly in the same direction as that of the first pipe member to the outer circumferential surface of said second pipe member to reflect back its echo therefrom; and
   calculating a size of a step fault produced at a bonding portion along the outer circumferential surface based on the reciprocating time of the outer reflected echo measured in said measurements;
      wherein said size of the step fault at the bonding portion along the outer circumferential surface $L_S$ is given by an expression, $$L_S = C_W \times (t_{S2} - t_{S1})/2,$$

where
   $C_W$: a propagation velocity with which the ultrasonic wave travels through a coupling medium intervening between said ultrasonic probe and the outer circumferential surface,
   $t_{S1}$: the reciprocating time of the outer reflected echo of the first pipe member of the metallic pipe, and
   $t_{S2}$: the reciprocating time of the outer reflected echo of the second pipe member of the metallic pipe.

6. A method for evaluating bonding properties of a metallic pipe, the method comprising steps of:
   measuring reciprocating time for an ultrasonic wave incident vertically to an outer circumferential surface of a first pipe member of the metallic pipe being bonded together by diffusion bonding to reflect back its echo from the outer circumferential surface and from an inner circumferential surface of said first pipe member of the metallic pipe;
   measuring reciprocating time for an ultrasonic wave incident vertically to an outer circumferential surface of a second member of said metallic pipe to reflect back its echo from the outer circumferential surface and from an inner circumferential surface of said second pipe member of the metallic pipe; and calculating a size of a step fault produced along the inner circumferential surface of a bonding portion from the reciprocating time of the outer reflected echo and the inner reflected echo measured in said measurements.

7. The method for evaluating bonding properties of a metallic pipe according to claim 6, wherein said size of the step fault along the inner circumferential surface of said bonding portion $L_B$ is given by an expression, $$L_B=(C_W-C_M)\times(t_{S2}-t_{S1})/2+C_M\times(t_{B2}-t_{B1}),$$

where $C_W$: a propagation velocity with witch an ultrasonic wave travels through a coupling medium intervening between an ultrasonic prove and the outer circumferential surface, $C_M$: a propagation velocity with witch an ultrasonic wave travels through said pipe members, $t_{S1}$: the reciprocating time of the outer reflected echo of said first pipe members, $t_{S2}$: the reciprocating time of the outer reflected echo of said second pipe member.

$t_{B1}$: the reciprocating time of the inner reflected echo of said first pipe member, and $t_{B2}$: the reciprocating time of the inner reflected echo of the second pipe member.

8. The method for evaluating bonding properties of a metallic pipe according to claim 6, wherein the reciprocating time of the outer reflected echo and the reciprocating time of the inner reflected echo are measured in a vicinity of said bonding portion in each of said measurements.

9. The method for evaluating bonding properties of a metallic pipe according to claim 6, wherein the reciprocating time of the outer reflected echo is measured in a vicinity of the bonding portion and the reciprocating time of the inner reflected echo is measured in a heat-unaffected portion in each of said measurements.

10. The method for evaluating bonding properties of a metallic pipe according to claim 6, further comprising a step of calculating a thickness of said bonding portion from the reciprocating time of the outer reflected echo and the reciprocating time of the inner reflected echo measured in each of said measurements.

11. The method for evaluating bonding properties of a metallic pipe according to claim 10, wherein said thickness of the bonding portion $D_1$ is given by an expression, $$L_A=D_2-D_1,$$

where $D_1$: one of $D_{S1}$ and $D_{S2}$ having a larger value than the other, where $D_{S1}$: a distance from the ultrasonic probe to said first pipe member=$C_W\times t_{S1}/2$, and $D_{S2}$: a distance from an ultrasonic probe to said second pipe member=$C_W\times t_{S2}/2$, and $D_2$: one of $(D_{S1}+T_{B1})$ and $(D_{S2}+T_{B2})$ having a smaller value than the other, where $T_{B1}$: a thickness of said first pipe member=$C_M\times(t_{S1}-t_{S1})/2$, and $T_{B2}$: a thickness of said second pipe member=$C_M\times(t_{B2}-t_{S2})/2$.

12. A method for evaluating bonding properties of a metallic pipe, the method comprising steps of:

measuring, in advance of a pipe expansion operation, at least one selected from a degree of shape discontinuity, a degree of defect at a bonding portion, and a degree of change in crystal structure, and comparing a measurement value with a predetermined threshold value to evaluate suitability of the bonding properties for applying pipe expansion.

13. The method for evaluating bonding properties of a metallic pipe according to claim 12, wherein said measurement comprises:

a first step of measuring said bonding portion of said metallic pipe for the degree of the shape discontinuity;

a second step of measuring said bonding portion for the degree of the defect; and a third step of measuring bonding portion for the degree of the defect; and the first step is carried out prior to the other steps.

14. The method for evaluating bonding properties of a metallic pipe according to claim 12, wherein said metallic pipe is bonded together by liquid diffusion bonding with an intervention of an insert material over bonding interfaces between pipe members to be bonded.

15. The method for evaluating bonding properties of a metallic pipe according to claim 12, wherein the form discontinuity of said bonding portion of said metallic pipe is evaluated based on time difference in detection of echo reflected from an outer surface and from an inner surface between each of said pipe members upon an ultrasonic wave incident to the outer surface of said pipe members adjacent to said bonding portion.

16. The method for evaluating bonding properties of a metallic pipe according to claim 12, wherein the degree of the defect at the bonding portion of said metallic pipe is evaluated based on an echo height reflected from a defect present at said bonding interfaces upon an ultrasonic wave incident toward both sides or one side of said bonding interfaces.

17. The method for evaluating bonding properties of a metallic pipe according to claim 12, wherein the degree of the change in the crystal structure is evaluated based on an echo height that has transmitted through said bonding portion upon an ultrasonic wave incident toward both sides or one side of said bonding interfaces.

* * * * *

UNITED STATES PATENT AND TRADEMARK OFFICE
CERTIFICATE OF CORRECTION

PATENT NO.    : 6,332,361 B1
DATED         : December 25, 2001
INVENTOR(S)   : Ryuzo Yamada et al.

It is certified that error appears in the above-identified patent and that said Letters Patent is hereby corrected as shown below:

Column 31,
Line 17, "witch" should read -- which --.
Line 19, "prove" should read -- probe --.
Line 21, "witch" should read -- which --.
Line 27, "member." should read -- member, --.

Column 32,
Lines 7-8, $C_M \times (t_{S1}-t_{S1})/2$" should read -- $C_M \times (t_{B1}-t_{S1})/2$ --.

Signed and Sealed this

Seventh Day of May, 2002

Attest:

Attesting Officer

JAMES E. ROGAN
Director of the United States Patent and Trademark Office